(12) United States Patent
Iding et al.

(10) Patent No.: US 7,122,562 B2
(45) Date of Patent: Oct. 17, 2006

(54) 4-PYRROLIDINO-PHENYL-BENZYL ETHER DERIVATIVES

(75) Inventors: Hans Iding, Rheinfelden (DE); Synese Jolidon, Blauen (CH); Daniela Krummenacher, Rheinfelden (CH); Rosa Maria Rodriguez-Sarmiento, Basle (CH); Andrew William Thomas, Birsfelden (CH); Beat Wirz, Reinach (CH); Wolfgang Wostl, Grenzach-Wyhlen (DE); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/325,747

(22) Filed: Jan. 5, 2006

(65) Prior Publication Data

US 2006/0122235 A1  Jun. 8, 2006

Related U.S. Application Data

(62) Division of application No. 10/667,088, filed on Sep. 18, 2003, now Pat. No. 7,037,935.

(30) Foreign Application Priority Data

Sep. 20, 2002  (EP) .................................. 02021319

(51) Int. Cl.
*A61K 31/4439* (2006.01)
*C07D 401/04* (2006.01)

(52) U.S. Cl. .................................... 514/343; 546/278.4
(58) Field of Classification Search ............... 514/343; 546/278.4

See application file for complete search history.

(56) References Cited

U.S. PATENT DOCUMENTS 4,287,351 A  9/1981  Bourgery et al.

FOREIGN PATENT DOCUMENTS

| EP | 0 393 607 | 10/1990 |
|---|---|---|
| FR | 2500831 | 9/1982 |
| WO | WO 96/40095 | 12/1996 |
| WO | WO 97/33572 | 9/1997 |
| WO | WO 01/34172 | 5/2001 |

OTHER PUBLICATIONS

Bach, et al. Proc. Natl. Acad. Sci. USA 85:4934-4938 (1988).
Cesura, et al., A., Prog. Drug Research 38:171-297 (1992).
Fowler, et al. J. Neural. Transm. 49:1-20 (1980).
Benedetti, et al. Biochem. Pharmacol. 38:555-561 (1989).
Saura, et al. Neuroscience 70:755-774 (1996).
Bentué-Ferrer, et al. CNS Drugs 6(3): 217-236 (1996).
Gardner, et al. J. Clin. Psychiatry 57(3):99-104 (1996).
Lam, et al. Tetrahedron Lett. 43:3091-3094 (2002).
Lam, et al. Synlett 5:674-676 (2000).
Chan, et al. Tetrahedron Lett. 39:2933-2936 (1998).
Wolfe, et al. J. Amer. Chem. Soc. 118:7215-7216 (1996).
Schlaeger, E. J., & Christensen, K., Cytotechnology 30:71-83 (1999).
Zhou, et al., Analytical Biochemistry 253:169-174 (1997).

*Primary Examiner*—Patricia L. Morris
(74) *Attorney, Agent, or Firm*—George W. Johnston; Patricia S. Rocha-Tramaloni; Kimberly J. Prior

(57) ABSTRACT

The invention relates to racemic or enantiomerically pure 4-pyrrolidino derivatives, processes for their preparation, pharmaceutical compositions comprising said derivatives, and their use in the prevention and treatment of illness, in particular which is mediated by monoamine oxidase B inhibitors, in particular Alzheimer's disease or senile dementia.

33 Claims, No Drawings

4-PYRROLIDINO-PHENYL-BENZYL ETHER DERIVATIVES

PRIORITY TO RELATED APPLICATIONS

This application is a division of U.S. application Ser. No. 10/667,088, filed Sep. 18, 2003 now U.S. Pat. No. 7,037,935; which claims the benefit of European Application No. 02021319.5, filed Sep. 20, 2002.

FIELD OF THE INVENTION

The present invention relates to new 4-pyrrolidino derivatives, to processes and intermediates for their preparation, and to pharmaceutical compositions containing them. These compounds are selective monoamine oxidase B inhibitors and, therefore, are useful for treating or preventing diseases mediated by monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethylamine, as well as a number of amine xenobiotics. The enzyme exists in two forms, MAO-A and MAO-B, encoded by different genes [Bach et al., Proc. Natl. Acad. Sci. USA 85:4934–4938 (1988)] and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain [Cesura and Pletscher, Prog. Drug Research 38:171–297 (1992)]. Brain MAO-B activity appears to increase with age. This increase has been attributed to the gliosis associated with aging [Fowler et al., J. Neural. Transm. 49:1–20 (1980)]. Additionally, MAO-B activity is significantly higher in the brains of patients with Alzheimer's disease [Dostert et al., Biochem. Pharmacol. 38:555–561 (1989)] and it has been found to be highly expressed in astrocytes around senile plaques [Saura et al., Neuroscience 70:755–774 (1994)]. In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B.

Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by Bentué-Ferrer et al. [CNS Drugs 6:217–236 (1996)]. Whereas a major limitation of irreversible and non-selective MAO inhibitor activity is the need to observe dietary precautions due to the risk of inducing a hypertensive crisis when dietary tyramine is ingested, as well as the potential for interactions with other medications [Gardner et al., J. Clin. Psychiatry 57:99–104 (1996)], these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The invention relates to racemic or enantiomerically pure 4-pyrrolidino derivatives, processes for their preparation, pharmaceutical compositions comprising said derivatives, and their use in the prevention and treatment of illness. More particularly, the present invention relates to compounds of the formula I

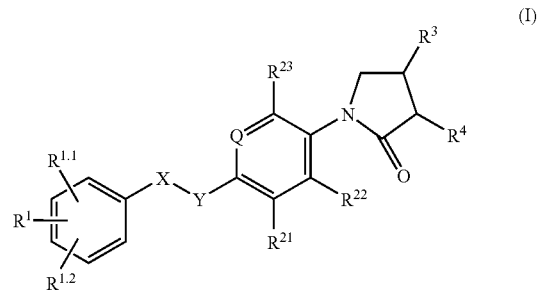

wherein Q is =N— or =C($R^{24}$)—; X—Y is —$CH_2$—$CH_2$—, —CH=CH— or —$CH_2$—O—; and $R^1$, $R^{1.1}$, $R^{1.2}$, $R^3$, $R^4$, $R^{21}$, $R^{22}$, and $R^{24}$ are as defined herein. The invention includes individual isomers of the compounds herein as well as racemic and non-racemic mixtures thereof.

It has been found that the compounds of general formula I and I* as well as individual isomers, racemic or non-racemic mixtures thereof (hereinafter: Active Compounds) are selective monoamine oxidase B inhibitors. Therefore, the invention relates to pharmaceutical compositions and methods for treating diseases mediated by MAO-B inhibitors, for example, Alzheimer's disease and senile dementia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

The term "individual isomers, racemic or non-racemic mixtures thereof" denotes E- and Z-isomers, mixtures thereof as well as individual configurational isomers and mixtures thereof.

The term "($C_1$–$C_6$)-alkyl" used in the present application denotes straight-chain or branched saturated hydrocarbon residues with 1 to 6 carbon atoms, such as methyl, ethyl, n-propyl, i-propyl, n-butyl, sec-butyl, t-butyl, and the like, preferably with 1 to 3 carbon atoms. Accordingly, the term "($C_1$–$C_3$)-alkyl" means a straight-chain or branched saturated hydrocarbon residue with 1 to 3 carbon atoms.

"$(C_1-C_6)$-Alkoxy" means the residue —O—R, wherein R is a lower alkyl residue as defined herein. Examples of alkoxy radicals include, but are not limited to, methoxy, ethoxy, isopropoxy, and the like.

The term "halogen" denotes fluorine, chlorine, bromine and iodine.

"Halogen-$(C_1-C_6)$-alkyl" or "halogen-$(C_1-C_6)$-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 3,3,3-trifluoropropyl, and the like. "Halogenalkoxy" includes trifluoromethyloxy.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base. If possible, Active Compounds may be converted into pharmaceutically acceptable salts. It should be understood that pharmaceutically acceptable salts are included in the present invention.

It should be understood that all references to pharmaceutically acceptable salts include solvent addition forms (solvates) or crystal forms (polymorphs) of the same acid addition salt.

"Therapeutically effective amount" means an amount that is effective to prevent, alleviate or ameliorate symptoms of disease or prolong the survival of the subject being treated.

The invention relates to racemic or enantiomerically pure 4-pyrrolidino derivatives, processes for their preparation, pharmaceutical compositions comprising said derivatives, and their use in the prevention and treatment of illness.

More particularly, the present invention relates to compounds of the formula I

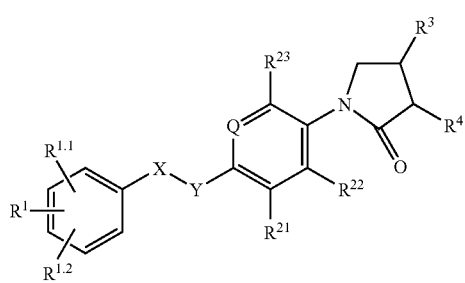

wherein
Q is =N— or =C($R^{24}$)—;
X—Y is —$CH_2$—$CH_2$—, —CH=CH— or —$CH_2$—O—;
$R^1$, $R^{1.1}$ and $R^{1.2}$ independently from each other are selected from the group consisting of hydrogen, halogen, $(C_1-C_6)$-alkyl, halogen-$(C_1-C_6)$-alkyl, cyano, $(C_1-C_6)$-alkoxy or halogen-$(C_1-C_6)$-alkoxy;
$R^{21}$, $R^{22}$ and $R^{23}$ independently from each other are selected from the group consisting of hydrogen and halogen;
$R^{24}$ is hydrogen, halogen or methyl;
$R^3$ is —C(O)N(H)$CH_3$ or —$CH_2$CN; and
$R^4$ is hydrogen;

as well as individual isomers, racemic or non-racemic mixtures thereof.

Even more particularly, the present invention relates to compounds of the formula I*

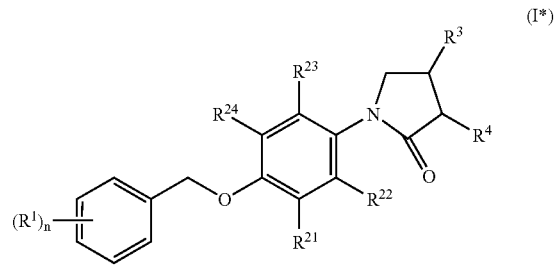

wherein
$R^1$ is halogen, halogen-$(C_1-C_6)$-alkyl, cyano, $(C_1-C_6)$-alkoxy or halogen-$(C_1-C_6)$ -alkoxy;
$R^{21}$, $R^{22}$, $R^{23}$ and $R^{24}$ independently from each other are selected from the group consisting of hydrogen and halogen;
$R^3$ is —CONH$R^5$, —$CH_2$CN or —CN;
$R^4$ is hydrogen;
$R^5$ is methyl; and
n is 0, 1, 2 or 3;

as well as individual isomers, racemic or non-racemic mixtures thereof.

A more preferred group of compounds of formula I* are those wherein $R^3$ is —CO—NH$R^5$ and $R^5$ is methyl.

Examples of such compounds are the following:
(RS)-1-[4-(3-fluoro-benzyloxy)-phenyl]-5-oxo-pyrrolidine-3-carboxylic acid methylamide,
(R)-1-[4-(3-fluoro-benzyloxy)-phenyl]-5-oxo-pyrrolidine-3-carboxylic acid methylamide,
(RS)-[1-[4-(3,4-difluoro-benzyloxy)-phenyl]-5-oxo-pyrrolidine-3-carboxylic acid methylamide,
(RS)-[1-[4-(2,6-difluoro-benzyloxy)-phenyl]-5-oxo-pyrrolidine-3-carboxylic acid methylamide,
(RS)-1-[4-(3-chloro-benzyloxy)-phenyl]-5-oxo-pyrrolidine-3-carboxylic acid methylamide,
(RS)-1-[3-fluoro-4-(3-fluoro-benzyloxy)-phenyl]-5-oxo-pyrrolidine-3-carboxylic acid methylamide,
(RS)-1-[2-fluoro-4-(3-fluoro-benzyloxy)-phenyl]-5-oxo-pyrrolidine-3-carboxylic acid methylamide,
(RS)-1-(4-benzyloxy-phenyl)-5-oxo-pyrrolidine-3-carboxylic acid methylamide, and
(R)-1-(4-benzyloxy-phenyl)-5-oxo-pyrrolidine-3-carboxylic acid methylamide.

A further preferred group of compounds of formula I* are those, wherein $R^3$ is —$CH_2$CN and $R^4$ is hydrogen. (RS)-1-[4-(3,4-difluoro-benzyloxy)-phenyl]-5-oxo-pyrrolidin-3-yl}-acetonitrile is an example for such a compound.

Compounds of formula I* may be substituted by n $R^1$ selected from the group consisting of halogen, halogen-$(C_1-C_6)$-alkyl, cyano, $(C_1-C_6)$-alkoxy or halogen-$(C_1-C_6)$ -alkoxy, wherein n denotes an integer selected from 0, 1, 2 and 3. Preferably n is 1 or 2.

Preferred compounds of formula I* are those, wherein $R^1$ is halogen or halogen-$(C_1-C_6)$-alkyl. Especially preferred are those compounds of formula I*, wherein $R^1$ is fluorine, chlorine or trifluoromethyl. Where the compounds are substituted by two or three $R^1$, each $R^1$ can be the same or different.

In one embodiment the invention provides compounds of formula I wherein Q is =C($R^{24}$)—, wherein $R^{24}$ is hydrogen, halogen or methyl. In another embodiment the invention provides compounds of formula I wherein Q is =CH—, =CF— or =C(CH$_3$)—. In still another embodiment the invention provides compounds of formula I wherein Q is =N—.

In one embodiment the invention provides compounds of formula I wherein —X—Y— is —CH$_2$—O—. In another embodiment the invention provides compounds of formula I wherein —X—Y— is —CH$_2$—CH$_2$— or —CH=CH—.

In one embodiment the invention provides compounds of formula I wherein $R^1$, $R^{1.1}$ and $R^{1.2}$ independently from each other are selected from the group consisting of hydrogen, halogen, methyl, halogenmethyl, cyano, methoxy or halogen-methoxy. In another embodiment the present invention provides compounds of formula I wherein $R^1$, $R^{1.1}$ and $R^{1.2}$ are halogen, e.g. fluoro, e.g. 2,4,6-trifluoro, 2,4,5-trifluoro, 2,3,6-trifluoro, 2,3,4-trifluoro or 3,4,5-trifluoro. In still another embodiment the present invention provides compounds of formula I wherein $R^{1.2}$ is hydrogen and $R^1$ and $R^{1.1}$ independently from each other are selected from the group consisting of hydrogen, halogen, (C$_1$–C$_6$)-alkyl, halogen-(C$_1$–C$_6$)-alkyl, cyano, (C$_1$–C$_6$)-alkoxy or halogen-(C$_1$–C$_6$)-alkoxy. In still another embodiment the present invention provides compounds of formula I wherein $R^{1.2}$ is hydrogen and $R^1$ and $R^{1.1}$ independently from each other are selected from the group consisting of halogen and (C$_1$–C$_6$)-alkyl. In still another embodiment the present invention provides compounds of formula I wherein $R^{1.2}$ is hydrogen, $R^{1.1}$ is halogen and $R^1$ is halogen or (C$_1$–C$_6$)-alkyl. In still another embodiment the present invention provides compounds of formula I wherein $R^{1.1}$ and $R^{1.2}$ are hydrogen and $R^1$ is halogen, (C$_1$–C$_6$)-alkyl, halogen-(C$_1$–C$_6$)-alkyl, cyano, (C$_1$–C$_6$)-alkoxy or halogen-(C$_1$–C$_6$)-alkoxy. In still another embodiment the present invention provides compounds of formula I wherein $R^{1.1}$ and $R^{1.2}$ are hydrogen and $R^1$ is halogen, methyl, halogenmethyl, cyano, methoxy or halogen-methoxy. In still another embodiment the present invention provides compounds of formula I wherein $R^{1.1}$ and $R^{1.2}$ are hydrogen and $R^1$ is fluoro, e.g. 3-fluoro or 4-fluoro, chloro, e.g. 3-chloro, halogenmethyl, e.g. 3-trifluoromethyl, cyano, methoxy, e.g. 2-methoxy, 3-methoxy or 4-methoxy, or halogen-methoxy, e.g. 3-trifluoromethoxy. In another embodiment the present invention provides compounds of formula I wherein $R^1$, $R^{1.1}$ and $R^{1.2}$ are hydrogen.

In one embodiment the present invention provides compounds of formula I wherein $R^{21}$, $R^{22}$ and $R^{23}$ are hydrogen. In another embodiment the present invention provides compounds of formula I wherein $R^{21}$ and $R^{23}$ are hydrogen and $R^{22}$ is fluoro.

In one embodiment the present invention provides compounds of formula I wherein $R^3$ is —C(O)N(H)CH$_3$. In another embodiment the present invention provides compounds of formula I wherein $R^3$ is —CH$_2$CN.

In one aspect the present invention provides compounds of formula I wherein the compounds have (R)-configuration.

In one embodiment the present invention provides compounds of formula I wherein Q is =C($R^{24}$)—, wherein $R^{24}$ is hydrogen, halogen or methyl; —X—Y— is —CH$_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; and $R^3$ is —C(O)N(H)CH$_3$.

In another embodiment the present invention provides compounds of formula I wherein Q is =CH—; —X—Y— is —CH$_2$—O—; $R^{21}$, $R^{22}$ and $R^{23}$ are hydrogen; and $R^3$ is —C(O)N(H)CH$_3$. In yet another embodiment, the invention provides compounds of formula I wherein Q is =CH—; —X—Y— is —CH$_2$—O—; $R^1$, $R^{1.1}$ and $R^{1.2}$ independently from each other are selected from the group consisting of hydrogen, halogen, methyl, halogenmethyl, cyano, methoxy or halogen-methoxy; $R^{21}$, $R^{22}$ and $R^{23}$ are hydrogen; and $R^3$ is —C(O)N(H)CH$_3$. In still another embodiment the present invention provides compounds of formula I wherein Q is =CH—; —X—Y— is —CH$_2$—O—; $R^{1.1}$ and $R^{1.2}$ are hydrogen and $R^1$ is fluoro, chloro, halogenmethyl, cyano, methoxy or halogen-methoxy; $R^{21}$, $R^{22}$ and $R^{23}$ are hydrogen; and $R^3$ is —C(O)N(H)CH$_3$.

Examples of compounds of formula I include compounds selected from (RS)-1-[4-(3-fluoro-benzyloxy)-phenyl]-5-oxo-pyrrolidine-3-carboxylic acid methylamide, (RS)-[1-[4-(4-fluoro-benzyloxy)-phenyl]-5-oxo-pyrrolidine-3-carboxylic acid methylamide, (RS)-1-[4-(3-chloro-benzyloxy)-phenyl]-5-oxo-pyrrolidine-3-carboxylic acid methylamide, (RS)-[1-[4-(3,4-difluoro-benzyloxy)-phenyl]-5-oxo-pyrrolidine-3-carboxylic acid methylamide, (RS)-[1-[4-(2,6-difluoro-benzyloxy)-phenyl]-5-oxo-pyrrolidine-3-carboxylic acid methylamide, (RS)-5-oxo-1-[4-(2,4,6-trifluoro-benzyloxy)-phenyl]-pyrrolidine-3-carboxylic acid methylamide, (RS)-5-oxo-1-[4-(2,4,5-trifluoro-benzyloxy)-phenyl]-pyrrolidine-3-carboxylic acid methylamide, (RS)-5-oxo-1-[4-(2,3,6-trifluoro-benzyloxy)-phenyl]-pyrrolidine-3-carboxylic acid methylamide, (RS)-5-oxo-1-[4-(2,3,4-trifluoro-benzyloxy)-phenyl]-pyrrolidine-3-carboxylic acid methylamide, (RS)-5-oxo-1-[4-(3,4,5-trifluoro-benzyloxy)-phenyl]-pyrrolidine-3-carboxylic acid methylamide, (RS)-1-[4-(5-fluoro-2-methyl-benzyloxy)-phenyl]-5-oxo-pyrrolidine-3-carboxylic acid methylamide, (RS)-1-[4-(3-methoxy-benzyloxy)-phenyl]-5-oxo-pyrrolidine-3-carboxylic acid methylamide, (RS)-1-[4-(2-methoxy-benzyloxy)-phenyl]-5-oxo-pyrrolidine-3-carboxylic acid methylamide, (RS)-5-oxo-1-[4-(3-trifluoromethoxy-benzyloxy)-phenyl]-pyrrolidine-3-carboxylic acid methylamide, (RS)-5-oxo-1-[4-(3-trifluoromethyl-benzyloxy)-phenyl]-pyrrolidine-3-carboxylic acid methylamide, (RS)-1-[4-(3-cyano-benzyloxy)-phenyl]-5-oxo-pyrrolidine-3-carboxylic acid methylamide, (RS)-1-[4-(3-fluoro-benzyloxy)-3-methyl-phenyl]-5-oxo-pyrrolidine-3-carboxylic acid methylamide, (RS)-1-[4-(4-fluoro-benzyloxy)-3-methyl-phenyl]-5-oxo-pyrrolidine-3-carboxylic acid methylamide, (RS)-1-[4-(3-chloro-benzyloxy)-3-methyl-phenyl]-5-oxo-pyrrolidine-3-carboxylic acid methylamide, (RS)-1-[3-fluoro-4-(3-fluoro-benzyloxy)-phenyl]-5-oxo-pyrrolidine-3-carboxylic acid methylamide, (RS)-1-[2-fluoro-4-(3-fluoro-benzyloxy)-phenyl]-5-oxo-pyrrolidine-3-carboxylic acid methylamide, (RS)-1-[2,5-difluoro-4-(3-fluoro-benzyloxy)-phenyl]-5-oxo-pyrrolidine-3-carboxylic acid methylamide, (RS)-1-(4-benzyloxy-phenyl)-5-oxo-pyrrolidine-3-carboxylic acid methylamide,
(R)-1-[4-(3-fluoro-benzyloxy)-phenyl]-5-oxo-pyrrolidine-3-carboxylic acid methylamide,
(S)-1-[4-(3-fluoro-benzyloxy)-phenyl]-5-oxo-pyrrolidine-3-carboxylic acid methylamide,
(R)-1-(4-benzyloxy-phenyl)-5-oxo-pyrrolidine-3-carboxylic acid methylamide,
(S)-1-(4-benzyloxy-phenyl)-5-oxo-pyrrolidine-3-carboxylic acid methylamide,
(R)-1-[4-(4-fluoro-benzyloxy)-phenyl]-5-oxo-pyrrolidine-3-carboxylic acid methylamide,
(R)-1-[4-(3-fluoro-benzyloxy)-phenyl]-5-oxo-pyrrolidine-3-carboxylic acid methylamide,
(R)-1-[4-(3-chloro-benzyloxy)-phenyl]-5-oxo-pyrrolidine-3-carboxylic acid methylamide,
(R)-1-[4-(2,6-difluoro-benzyloxy)-phenyl]-5-oxo-pyrrolidine-3-carboxylic acid methylamide,
(R)-5-oxo-1-[4-(2,4,6-trifluoro-benzyloxy)-phenyl]-pyrrolidine-3-carboxylic acid methylamide,
(RS)-1-[4-(3,4-difluoro-benzyloxy)-phenyl]-5-oxo-pyrrolidin-3-yl}-acetonitrile,
(RS)-{1-[4-(3-fluoro-benzyloxy)-phenyl]-5-oxo-pyrrolidin-3-yl}-acetonitrile,
(RS)-[1-(4-benzyloxy-phenyl)-5-oxo-pyrrolidin-3-yl]-acetonitrile,
(RS)-(E)-1-{4-[2-(3-fluoro-phenyl)-vinyl]-phenyl}-5-oxo-pyrrolidine-3-carboxylic acid methylamide,
(RS)-(E)-1-{4-[2-(4-methoxy-phenyl)-vinyl]-phenyl}-5-oxo-pyrrolidine-3-carboxylic acid methylamide,
(RS)-(E)-1-{4-[2-(3-methoxy-phenyl)-vinyl]-phenyl}-5-oxo-pyrrolidine-3-carboxylic acid methylamide,
(RS)-(E)-1-{4-[2-(4-fluoro-phenyl)-vinyl]-phenyl}-5-oxo-pyrrolidine-3-carboxylic acid methylamide,
(RS)-1-{4-[2-(3-chloro-phenyl)-ethyl]-phenyl}-5-oxo-pyrrolidine-3-carboxylic acid methylamide,
(RS)-1-{4-[2-(4-chloro-phenyl)-ethyl]-phenyl}-5-oxo-pyrrolidine-3-carboxylic acid methylamide,
(RS)-1-{4-[2-(3-fluoro-phenyl)-ethyl]-phenyl}-5-oxo-pyrrolidine-3-carboxylic acid methylamide,
(RS)-1-{4-[2-(4-fluoro-phenyl)-ethyl]-phenyl}-5-oxo-pyrrolidine-3-carboxylic acid methylamide,
(RS)-1-{4-[2-(3-methoxy-phenyl)-ethyl]-phenyl}-5-oxo-pyrrolidine-3-carboxylic acid methylamide,
(RS)-1-[6-(4-fluoro-benzyloxy)-pyridin-3-yl]-5-oxo-pyrrolidine-3-carboxylic acid methylamide, and
(RS)-1-[4-(2-fluoro-benzyloxy)-phenyl]-5-oxo-pyrrolidine-3-carboxylic acid methylamide.

In another embodiment the present invention provides a process for the preparation of compounds of formula I comprising reacting a compound of formula II wherein $R^1$, $R^{1.1}$, $R^{1.2}$, $R^{21}$, $R^{22}$, $R^{23}$, $R^4$, —X—Y— and Q have the above meanings and R* is hydrogen or $(C_1-C_6)$-alkyl (a) with an amine of formula $H_2N$—$CH_3$, obtaining compounds of formula I wherein $R^3$ is —C(O)N(H)CH$_3$; or
(b) reducing a compound of formula II to a compound of formula III

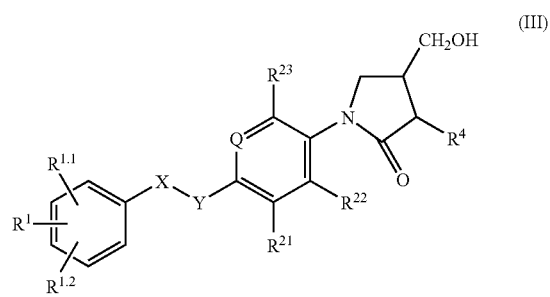

wherein $R^1$, $R^{1.1}$, $R^{1.2}$, $R^{21}$, $R^{22}$, $R^{23}$, $R^4$, —X—Y— and Q have the above meanings and reacting this compound with a cyanide salt, obtaining compounds of formula I wherein $R^3$ is $CH_2CN$.

The compounds of general formula I* can be manufactured by reacting a compound of formula II* wherein $R^1$, $R^{21}$, $R^{22}$, $R^{23}$, $R^{24}$ and n have the above meanings with an amine of formula $H_2N$—$R^5$, wherein $R^5$ has the above meaning, to obtain a compound of formula Ia* or, alternatively, reducing a compound of formula II* to the corresponding alcohol of formula III* and reacting this compound with a cyanide salt to obtain a compound of formula Ib*

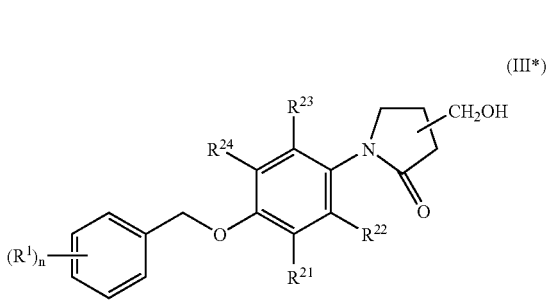

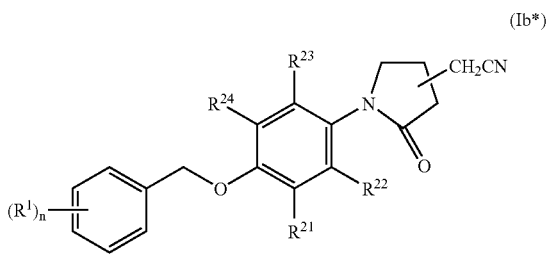

or, alternatively, reacting a compound of formula IV*

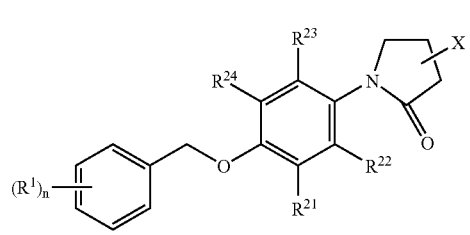

wherein X is halogen, with a cyanide salt, to obtain a compound of formula Ic*

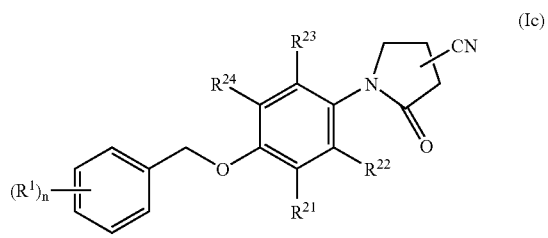

All starting materials employed in the processes described herein are either commercially available or can be prepared by conventional means.

In accordance with the present invention, scheme 1 shows the main routes to compounds of the formula I wherein $R^3$ is —C(O)N(H)CH$_3$, i.e. compounds of formula I**.

The reaction of the intermediates IV and IVa with itaconic acid V is preferentially done neat at temperatures between 80° C. and 200° C. Compounds of formula Ia and IVa are then transformed to esters of formula IIb and VIa by methods known per se.

Compounds of formula VIa can then be alkylated by Williamson-ether synthesis using optionally substituted benzylic halides, tosylates, mesylates or triflates. Bases used can be, e.g., alcoholates or carbonates, like e.g. sodium, potassium or cesium carbonate. Examples for solvents are lower alcohols, acetonitrile or lower ketones. The temperature may be, e.g. in the range of from 20° C. to reflux temperature. Another approach is the Mitsunobu-coupling of optionally substituted benzylic alcohols with phenol VIa. The reaction may be done as usual in inert solvents, e.g., diethyl ether or tetrahydrofurane, using dialkyl-azo-dicarboxylates in the presence of phosphines (e.g. tributyl- or triphenyl-phosphine). The hydrolysis of compounds of formula VIa can be performed by methods known per se like hydrolysis under acidic conditions, e.g. with hydrochloric acid, or basic conditions, e.g. lithium, sodium- or potassium hydroxide in mixtures of alcohols and water as the solvent.

In compounds of formula I** or IIb where —X—Y— has the meaning of —CH$_2$—O—, the optionally substituted benzyl residue can function as a transient group which can be cleaved by hydrogenolysis. The resulting phenols VIa and VIb can then be re-alkylated by a different benzyl group under the aforementioned conditions. As known to those skilled in the art, this process is only possible on condition that the other substituents are stable under the aforementioned reaction conditions for the hydrogenolysis and alkylation reaction, eg. formyl or acetyl for $R^6$, tert-butoxycarbonyl (BOC) for PG.

Scheme 1

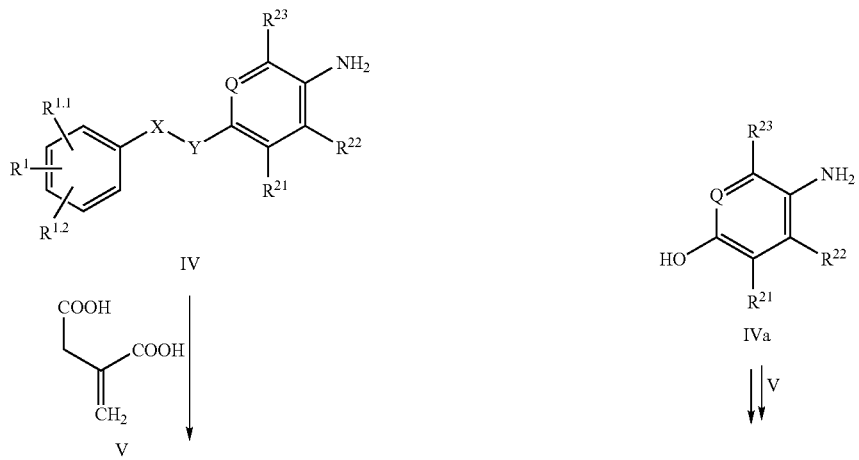

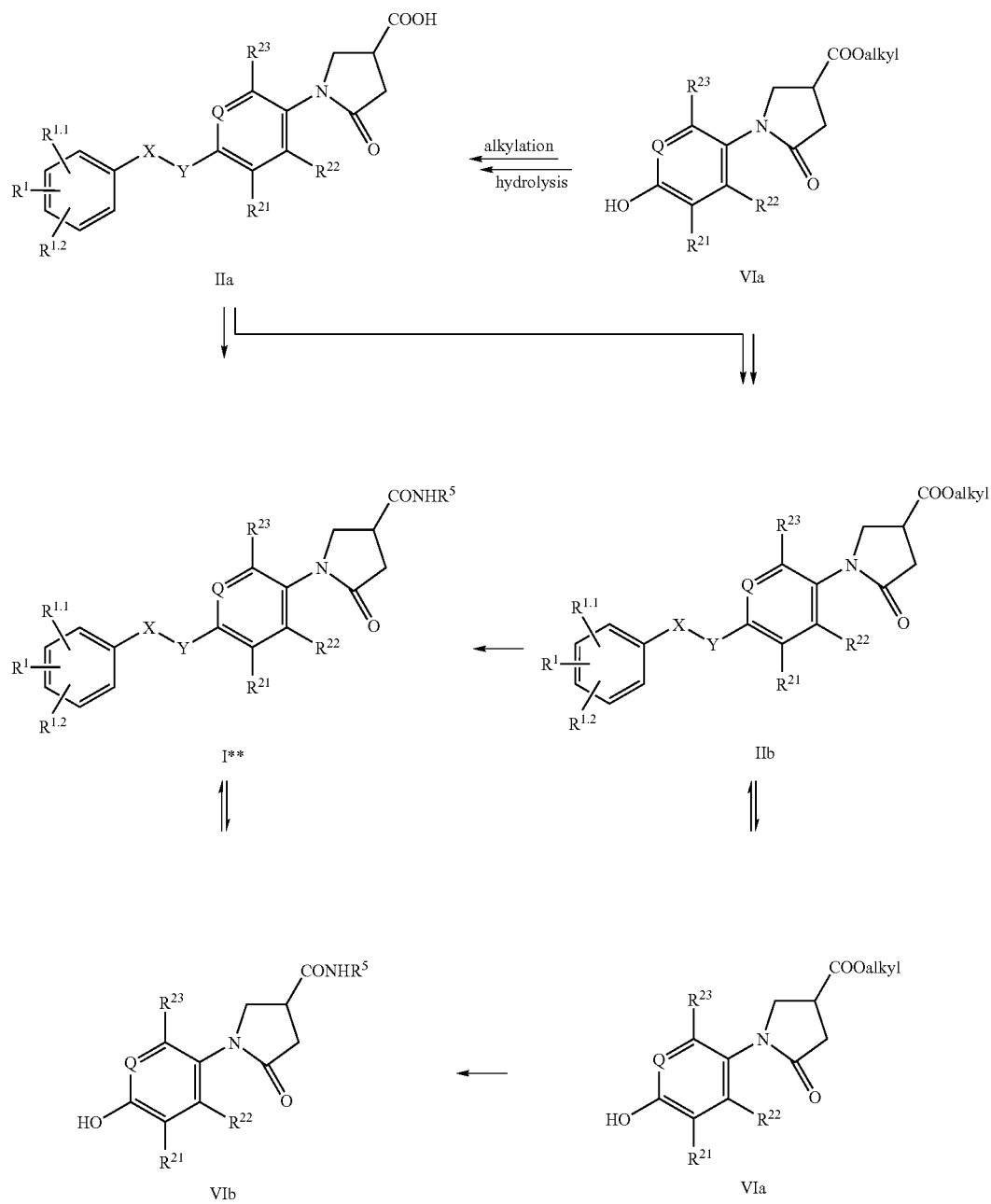

Amides of formula I or VIb can be obtained by aminolysis of esters of formula IIb or VIa with amines of formula R₅—NH₂ at a temperature in the range of from room temperature (RT) and 120° C., e.g. in sealed tubes using solvents inert under these conditions, like e.g. dimethoxyethane, dioxane, or methanol. Alternatively, acids of formula IIa may be transformed into compounds of formula I using standard procedures. They can be activated via, e.g., acid chloride or mixed anhydride. Especially for the preparation of enantiopure derivatives, condensation reagents like carbodiimides, e.g. dicyclohexyl-carbodiimide, or benzotriazol derivatives, e.g. O-(benzotriazol-1-yl)-N,N,N',N'-tetramethyluronium-hexafluorophosphate (HBTU) may be applied.

Another method to prepare compounds of formula I involves cross-coupling reactions of arylstannanes [Lam et al., Tetrahedron Lett. 43:3091 (2002)], arylboronates [Lam et al., Synlett 5:674 (2000); Chan et al., Tetrahedron Lett. 39:2933 (1998)] or aryl halides [Buchwald et al., J. Amer. Chem. Soc. 118:7215 (1996)] with the corresponding pyrrolidones (scheme 2).

Scheme 2 wherein LG is a leaving group, e.g. halogen, e.g. Cl, Br or I, or $SnR_3$ or $B(OH)_2$, and $R^{3'}$ is —$CONHR^5$ or —$CH_2CN$ or alkoxycarbonyl.

In accordance with the present invention, one method to prepare the intermediates of general formula IV, wherein —X—Y— is —$CH_2$—O—, i.e. a compound of formula IVb, is shown in scheme 3: The intermediates of formula XII are accessible through nucleophilic substitution of aromatic nitro compounds of formula XI containing p-substituted leaving groups with benzylic alcohols of formula X. Leaving groups in para-position can be, e.g., halogens (F, Cl, Br, I), tosylates, mesylates or triflates. These substitution reactions can be conducted neat or in inert solvents, e.g., toluene or xylene. The reaction temperature may be in the range of from 50° C. to 150° C. Alternatively, compounds of formula XII can be prepared by Williamson-ether synthesis, starting from p-nitrophenols of formula XIV and benzylic halides, tosylates, mesylates or triflates of formula XIII. Bases used can be, e.g., alcoholates or carbonates (sodium, potassium or cesium carbonate). Examples for solvents are lower alcohols, acetonitrile or lower ketones. The temperature may be in the range of from 20° C. to reflux temperature. Another approach is the Mitsunobu-coupling of benzylic alcohols with p-nitrophenols of formula XIV. The reaction is done as usual in inert solvents like for example diethyl ether or tetrahydrofurane, using dialkyl azo-dicarboxylates in the presence of phosphines like e.g. tributyl- or triphenyl-phosphine.

The key intermediates of formula XII are reduced to the amino compounds of formula IVb using catalytic hydrogenation, like e.g. using platinum on charcoal as the catalyst in lower alcohols, ethyl acetate or tetrahydrofurane. An alternative is the reduction of the nitro-group by metals like iron, tin, or zinc in acidic media, like diluted hydrochloric acid or acetic acid. Metals can also be replaced by metal salts like e.g. tin-(II)-chloride.

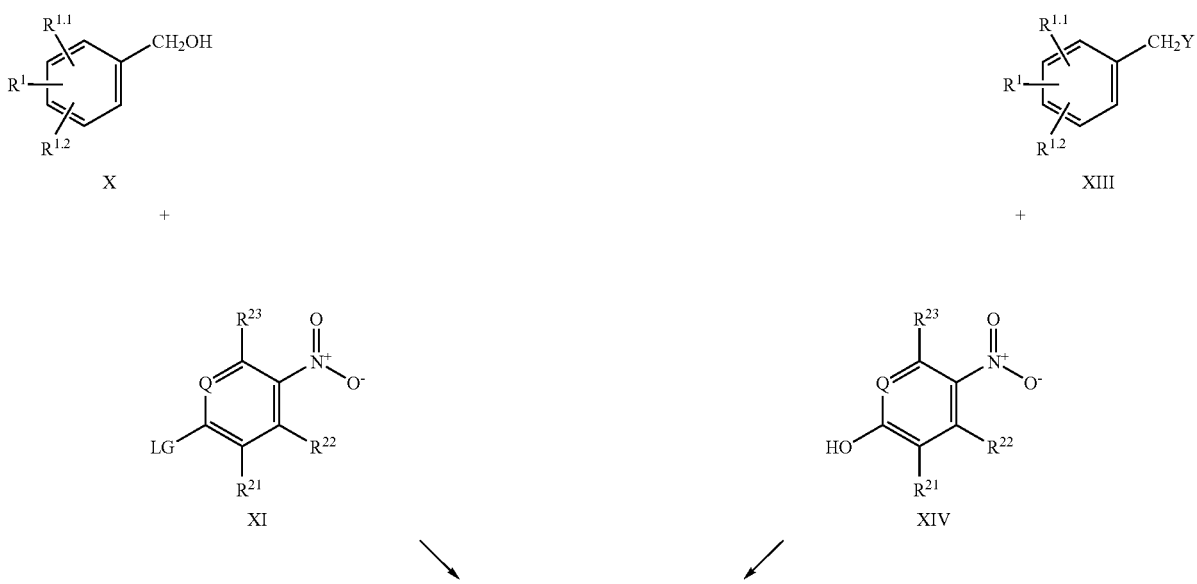

Scheme 3

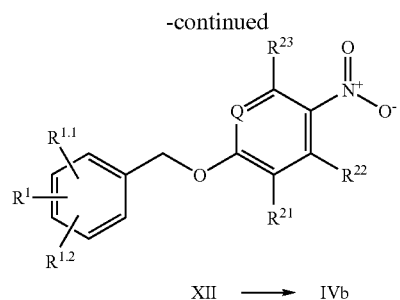

XII → IVb wherein LG is a leaving group, e.g. halogen, OTf, etc., and Y is a leaving group, e.g. halogen, OTf, etc. or OH (for Mitsunobu-coupling).

In accordance with the present invention, one method to prepare the intermediates of formula IVd (wherein —X—Y— is —CH=CH—) and IVc (wherein —X—Y— is —CH$_2$—CH$_2$—) is shown in scheme 4: The intermediates of formula XVII are accessible by olefination reaction of optionally substituted aromatic aldehydes of formula XV with dialkyl (4-nitro-benzyl)-phosphonates of formula XVI in the presence of a base, like e.g. sodium hydride, yielding the corresponding nitro-olefins of formula XVII.

tin-(II)-chloride. The amino derivatives of formula IVc can be obtained directly from the nitro derivatives of formula XVII or from the amino-olefins of formula IVd by hydrogenation using palladium on charcoal as the catalyst in lower alcohols, ethyl acetate or tetrahydrofurane as the solvent.

Alternatively, compounds of formula II can be reduced to the intermediate compound of formula III. This may be done by first converting the acids of formula II into their esters (alcohol/acid catalysis) followed by reduction with reagents like sodium borohydride in solvents like tetrahydrofurane at a temperature in the range of from 20° C. to 65° C.

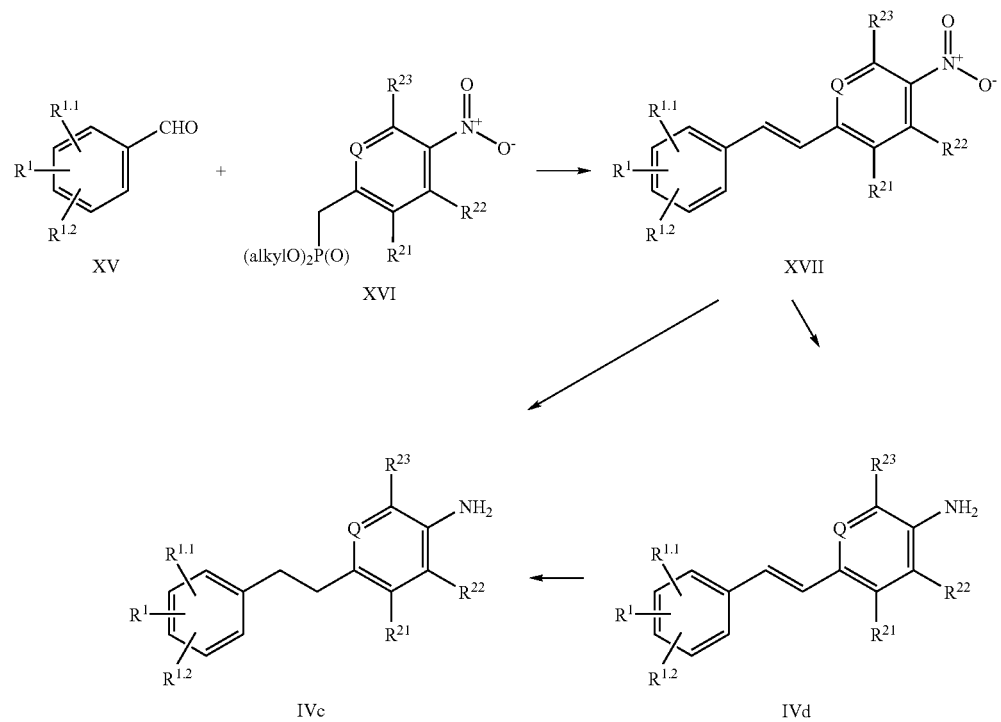

Scheme 4

The key intermediates of formula XVII can be reduced selectively to the amino-olefins of formula IVd using catalytic hydrogenation like e.g. using platinum on charcoal as the catalyst in lower alcohols, ethyl acetate or tetrahydrofurane as the solvent, or, by metals or metal salts, like e.g.

Activation of the alcohol of formula III via mesylate or triflate and reaction with sodium or potassium cyanide at a temperature in the range of from 40° C. to 80° C. leads to the desired compounds of formula I wherein R$^3$ is CH$_2$CN, i.e. nitriles of formula Ib.

Scheme 5

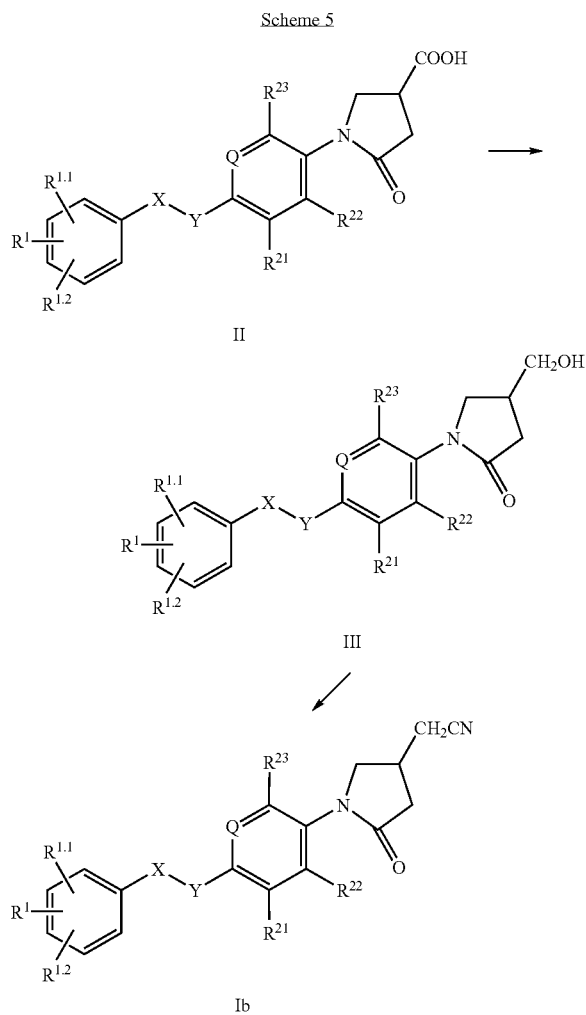

Compounds of general formula I can also exist in optical pure form. Separation into antipodes can be affected according methods known per se, either at an early stage of the synthesis, e.g. starting with compounds of formula Ia by salt formation with an optically active amine such as, for example, (+)- or (−)-1-phenylethylamine or (+)- or (−)-1-naphthylethylamine and separation of the diastereomeric salts by fractional crystallisation, or by derivatisation with a chiral auxiliary substance such as, for example, (+)- or (−)-2-butanol, (+)- or (−)-1-phenylethanol, or (+)- or (−)-menthol and separation of the diastereomeric products by chromatography and/or crystallisation and subsequent cleavage of the bond to the chiral auxiliary substance; or, on the very last stage, by separation of the enantiomers of formula I by chromatography on a chiral phase.

Furthermore, compounds of formula I can also be obtained from enantiopure intermediates obtained by biotransformation, e.g. by hydrolysis of esters of formula VIa by enzymes, such as e.g. cholesterase from *Candida cylindracea*. In order to determine the absolute configuration of the pyrrolidinone derivative obtained, the pure diastereomeric salts or derivatives can be analysed by conventional spectroscopic methods, e.g. with X-ray spectroscopy on single crystals.

The Active Compounds are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease.

Other indications include psychiatric diseases such as depression, anxiety, panic attack, social phobia, schizophrenia, eating and metabolic disorders such as obesity, as well as the prevention and treatment of withdrawal syndromes induced by abuse of alcohol, nicotine and other addictive drugs. Other treatable indications may be peripheral neuropathy caused by cancer chemotherapy (WO 97/33,572), reward deficiency syndrome (WO 01/34,172), or the treatment of multiple sclerosis (WO 96/40,095), and other neuroinflammatory diseases.

The Active Compounds are especially useful for the treatment and prevention of Alzheimer's disease and senile dementia.

The pharmacological activity of the compounds was tested using the following method:

The cDNAs encoding human MAO-A and MAO-B were transiently transfected into EBNA cells using the procedure described by Schlaeger and Christensen [Cytotechnology 15:1–13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing steps with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169–174 (1997)]. Briefly, membrane aliquots were incubated in 0.1 M potassium phosphate buffer, pH 7.4, for 30 min at 37° C. containing different concentrations of the compounds. After this period, the enzymatic reaction was started by the addition of the MAO substrate tyramine together with 1 U/ml horse-radish peroxidase (Roche Biochemicals) and 80 μM N-acetyl-3,7-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B. $IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of preferred Active Compounds as measured in the assay described above are in the range of 1 μM or less, typically 0.1 μM or less, and ideally 0.02 μM or less.

The present invention also provides pharmaceutical compositions containing Active Compounds, or pharmaceutically acceptable salts thereof, and a pharmaceutically acceptable carrier. Active Compounds include individual isomers and racemic and non-racemic mixtures thereof. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more Active Compounds, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of Active Compounds, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

Compounds of the invention are selective MAO-B inhibitors. Therefore, the present invention also provides methods of treating or preventing diseases that are mediated by monoamine oxidase B. Such methods include administering a therapeutically effective amount of an Active Compound, for example, a compound of formula I or I*, or a pharmaceutically acceptable salt thereof, to an individual in need of such treatment. In one embodiment, the invention provides a method for the treatment or prevention of Alzheimer's disease by administering to an individual a therapeutically effective amount of an Active Compound, e.g., a compound of formula I or I*. In another embodiment, the present invention provides a method for the treatment or prevention of senile dementia by administering to an individual a therapeutically effective amount of an Active Compound, e.g., a compound of formula I or I*.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

The dosage at which the Active Compound is administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof. Unless otherwise indicated, the following examples have been performed, regardless of the tense in which they are written. The abbreviation "RT" means "room temperature."

EXAMPLE 1

(RS)-1-[4-(3-Fluoro-benzyloxy)-phenyl]-5-oxo-pyrrolidine-3-carboxylic acid methylamide a) (RS)-1-(4-Benzyloxy-phenyl)-5-oxo-pyrrolidine-3-carboxylic acid 18.8 g (94.4 mmol) 4-benzyloxyaniline are mixed with 12.28 g (94.4 mmol) itaconic acid. The mixture is heated to 130° C. After 20 min the melted material solidifies. The resulting solid is triturated with ethyl acetate to yield 28.26 g (96%) of a greyish solid. MS: m/e=311 (M$^+$).

b) (RS)-1-(4-Benzyloxy-phenyl)-5-oxo-pyrrolidine-3-carboxylic acid methyl ester 7.46 g (24 mmol) (RS)-1-(4-benzyloxy-phenyl)-5-oxo-pyrrolidine-3-carboxylic acid is dissolved in a mixture of 40 ml dichloromethane and 7.5 ml methanol. 0.13 ml concentrated sulfuric acid is added and the reaction mixture hold under reflux over night. The solvent is evaporated and the residue triturated with diethyl ether to yield 7.26 g (93%) of a colorless solid (used in the next step without further purification).

c) (RS)-1-(4-Hydroxy-phenyl)-5-oxo-pyrrolidine-3-carboxylic acid methyl ester 7.26 g (22.3 mmol) (RS)-1-(4-benzyloxy-phenyl)-5-oxo-pyrrolidine-3-carboxylic acid methyl ester is dissolved in 200 ml tetrahydrofuran. After addition of 726 mg palladium 10% on charcoal hydrogenation is performed at RT and normal pressure. After 3 hours, the catalyst is filtered off and the solvent evaporated to yield 6.04 g of crude product (used in the next step without further purification).

d) (RS)-1-[4-(3-Fluoro-benzyloxy)-phenyl]-5-oxo-pyrrolidine-3-carboxylic acid methyl ester 6.04 g (RS)-1-(4-hydroxy-phenyl)-5-oxo-pyrrolidine-3-carboxylic acid methyl ester, 7.10 g (51.4 mmol) potassium carbonate and 5.34 g 3-fluorobenzyl bromide are suspended in 250 ml ethyl methyl ketone. The reaction mixture is heated at 90° C. for 5 hours, cooled and poured into water. Extraction with ethyl acetate gives a crude material which is subjected to chromatography (silica gel, n-hexane/ethyl acetate 1:1). This gives 2.10 g (24%) of a colorless solid. MS: m/e=344.3 (M+H)$^+$.

e) (RS)-1-[4-(3-Fluoro-benzyloxy)-phenyl]-5-oxo-pyrrolidine-3-carboxylic acid methylamide 300 mg (0.87 mmol) (RS)-1-[4-(3-fluoro-benzyloxy)-phenyl]-5-oxo-pyrrolidine-3-carboxylic acid methyl ester is dissolved in a mixture of 1 ml N,N-dimethylformamide and 0.18 ml of a 33% solution of methylamine in ethanol. The reaction vessel is tightly stopped and hold at 120° C. for 48 hours. Water is added and the product extracted with ethyl acetate. Drying and evaporation yields 92 mg (31%) of a slightly yellowish product. MS: m/e=343.3 (M+H)$^+$.

EXAMPLE 2

(RS)-[1-[4-(4-Fluoro-benzyloxy)-phenyl]-5-oxo-pyrrolidine-3-carboxylic acid methylamide a) (RS)-1-(4-Hydroxyoxy-phenyl)-5-oxo-pyrrolidine-3-carboxylic acid

In a metallic pan, 257.0 g (2.355 mol) of 4-aminophenol and 301.75 g (2.32 mol) of itaconic acid are mixed in solid form. Under stirring with a metal spatula, the mixture was carefully heated on a heating plate. The temperature was measured by a thermometer. At 60° C., the powder started to become viscous, at 110–120° C. it became liquid and the color turned to dark brown while the rest of solid material was also dissolved. The exothermic reaction started under boiling and, while the temperature raised to 150° C., the reaction mass turned to a beige solid. The sandy product was left to cool down to RT within 1–2 hours. The crude (RS)-1-(4-hydroxyoxy-phenyl)-5-oxo-pyrrolidine-3-carboxylic acid was engaged in the next step without further purification or characterisation.

b) (RS)-1-(4-Hydroxy-phenyl)-5-oxo-pyrrolidine-3-carboxylic acid methyl ester In a 10 14-necked flask equipped with a reflux condenser, a thermometer, and a mechanical stirrer, the crude (RS)-1-(4-hydroxyoxy-phenyl)-5-oxo-pyrrolidine-3-carboxylic acid is dissolved in a mixture of 5000 ml of methanol, 24 ml of concentrated sulfuric acid and 400 ml of 2,2-dimethoxypropane and stirred under reflux during 2 h. For the working-up, the reaction solution is reduced to half of its volume by distillation, then transferred into a 20 l vessel. Under stirring at 40° C., a mixture of 2500 ml of water/ice (1:1) is added. Crystallisation started immediately, and, thereupon, the fine white crystals are collected on a filter funnel. They are washed with total 2000 ml of cold water until the filtrate, at the beginning brownish-rose, becomes colorless and neutral. The well pressed and pre-dried product from the filter funnel is dried under reduced pressure to yield 980 g (84% of theory, 2 steps) of the (RS)-1-(4-hydroxyoxy-phenyl)-5-oxo-pyrrolidine-3-carboxylic acid methyl ester as a white solid; MS: m/e=234 (M+H)$^+$.

c) (RS)-1-[4-(4-Fluoro-benzyloxy)-phenyl]-5-oxo-pyrrolidine-3-carboxylic acid methyl ester In an analogous manner to that described in Example 1d), the alkylation of the (RS)-1-(4-hydroxyoxy-phenyl)-5-oxo-pyrrolidine-3-carboxylic acid methyl ester with 4-fluorobenzylbromide in presence of potassium carbonate yields the (RS)-1-[4-(4-fluoro-benzyloxy)-phenyl]-5-oxo-pyrrolidine-3-carboxylic acid methyl ester as a light yellow powder; MS: m/e=344 (M+H)$^+$.

d) (RS)-1-[4-(4-Fluoro-benzyloxy)-phenyl]-5-oxo-pyrrolidine-3-carboxylic acid methylamide In an analogous manner to that described in Example 1e), the aminolysis of the (RS)-1-[4-(4-fluoro-benzyloxy)-phenyl]-5-oxo-pyrrolidine-3-carboxylic acid methyl ester with methylamine in a sealed tube at 80° C. in ethanol during 18 h yields the (RS)-1-[4-(4-fluoro-benzyloxy)-phenyl]-5-oxo-pyrrolidine-3-carboxylic acid methylamide as a white powder; MS: m/e=343 (M+H)$^+$.

The compounds of Examples 3 to 16 are obtained in an analogous manner to that described in Example 1d) and e), starting from (RS)-1-(4-hydroxyphenyl)-5-oxo-pyrrolidine-3-carboxylic acid methyl ester, prepared following Example 1c) or Example 2b), by alkylation of the phenol and subsequent aminolysis of the ester:

EXAMPLE 3

(RS)-1-[4-(3–Chloro-benzyloxy)-phenyl]-5-oxo-pyrrolidine-3-carboxylic acid methylamide In an analogous manner to that described in Example 1d) and e), starting from (RS)-1-(4-hydroxyphenyl)-5-oxo-pyrrolidine-3-carboxylic acid methyl ester [Example 1c)] the title compound is prepared by alkylation with 3-chlorobenzyl chloride to obtain the (RS)-1-[4-(3-chloro-benzyloxy)-phenyl]-5-oxo-pyrrolidine-3-carboxylic acid methyl ester as a colorless solid and, thereupon, treatment with methylamine in ethanol at 80° C. during 18 h to yield the (RS)-1-[4-(3-chloro-benzyloxy)-phenyl]-5-oxo-pyrrolidine-3-carboxylic acid methylamide. Yield: 73% of a colorless solid. MS: m/e=359 (M+H)$^+$.

EXAMPLE 4

(RS)-[1-[4-(3,4-Difluoro-benzyloxy)-phenyl]-5-oxo-pyrrolidine-3-carboxylic acid methylamide In an analogous manner to that described in Example 1d) and e), starting from (RS)-1-(4-hydroxyphenyl)-5-oxo-pyrrolidine-3-carboxylic acid methyl ester [Example 1c)] the title compound is prepared by alkylation with 3,4-difluorobenzyl bromide to obtain the (RS)-1-[4-(3,4-difluoro-benzyloxy)-phenyl]-5-oxo-pyrrolidine-3-carboxylic acid methyl ester as a colorless solid [85% of theory; MS: m/e=362.2 (M$^+$+H)] and, thereupon, treatment with methylamine to yield the (RS)-[1-[4-(3,4-difluoro-benzyloxy)-phenyl]-5-oxo-pyrrolidine-3-carboxylic acid methylamide. Yield: 7% of a colorless solid. MS: m/e=361 (M+H)$^+$.

EXAMPLE 5

(RS)-[1-[4-(2,6-Difluoro-benzyloxy)-phenyl]-5-oxo-pyrrolidine-3-carboxylic acid methylamide In an analogous manner to that described in Example 1d) and e), starting from (RS)-1-(4-hydroxyphenyl)-5-oxo-pyrrolidine-3-carboxylic acid methyl ester [Example 1c)] the title compound is prepared by alkylation with 2,6-difluorobenzyl bromide to obtain the (RS)-1-[4-(2,6-difluoro-benzyloxy)-phenyl]-5-oxo-pyrrolidine-3-carboxylic acid methyl ester as a yellowish oil and, thereupon, treatment with methylamine in ethanol at 80° C. during 18 h to yield the (RS)-[1-[4-(2,6-difluoro-benzyloxy)-phenyl]-5-oxo-pyrrolidine-3-carboxylic acid methylamide. Yield: 33% of a colorless solid. MS: m/e=361 (M+H)$^+$.

EXAMPLE 6

(RS)-5-Oxo-1-[4-(2,4,6-trifluoro-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 2,4,6-trifluorobenzyl bromide giving the (RS)-5-oxo-1-[4-(2,4,6-trifluoro-benzyloxy)-phenyl]- pyrrolidine-3-carboxylic acid methyl ester which, thereupon, by treatment with methylamine yields the (RS)-5-oxo-1-[4-(2,4,6-trifluoro-benzyloxy)-phenyl]-pyrrolidine-3-carboxylic acid methylamide. Yield: 97% of theory as a white solid. MS: m/e=379 (M+H)⁺.

EXAMPLE 7

(RS)-5-Oxo-1-[4-(2,4,5-trifluoro-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 2,4,5-trifluorobenzyl bromide giving the (RS)-5-oxo-1-[4-(2,4,5-trifluoro-benzyloxy)-phenyl]-pyrrolidine-3-carboxylic acid methyl ester as a white solid (83% of theory) which, thereupon, by treatment with methylamine yields the (RS)-5-oxo-1-[4-(2,4,5-trifluoro-benzyloxy)-phenyl]-pyrrolidine-3-carboxylic acid methylamide as a light yellow solid; MS: m/e=379 (M+H)⁺.

EXAMPLE 8

(RS)-5-Oxo-1-[4-(2,3,6-trifluoro-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 2,3,6-trifluorobenzyl bromide giving the (RS)-5-oxo-1-[4-(2,3,6-trifluoro-benzyloxy)-phenyl]-pyrrolidine-3-carboxylic acid methyl ester as a light yellow solid [73% of theory, MS: m/e=379 (M+H)⁺], which, thereupon, by treatment with methylamine yields the (RS)-5-oxo-1-[4-(2,3,6-trifluoro-benzyl-oxy)-phenyl]-pyrrolidine-3-carboxylic acid methylamide. Yield: 64% of theory as a white solid. MS: m/e=379 (M+H)⁺.

EXAMPLE 9

(RS)-5-Oxo-1-[4-(2,3,4-trifluoro-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 2,3,4-trifluorobenzyl bromide giving the (RS)-5-oxo-1-[4-(2,3,4-trifluoro-benzyloxy)-phenyl]-pyrrolidine-3-carboxylic acid methyl ester as a white solid (94% of theory) which, thereupon, by treatment with methylamine in ethanol at 50° C. yields the (RS)-5-oxo-1-[4-(2,3,4-trifluoro-benzyloxy)-phenyl]-pyrrolidine-3-carboxylic acid methylamide. Yield: 99% of theory as a white solid; MS: m/e=379 (M+H)⁺.

EXAMPLE 10

(RS)-5-Oxo-1-[4-(3,4,5-trifluoro-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 2,4,6-trifluorobenzyl bromide giving the (RS)-5-oxo-1-[4-(3,4,5-trifluoro-benzyloxy)-phenyl]-pyrrolidine-3-carboxylic acid methyl ester as a white solid (99% of theory) which, thereupon, by treatment with methylamine in ethanol at 50° C. yields the (RS)-5-oxo-1-[4-(3,4,5-trifluoro-benzyloxy)-phenyl]-pyrrolidine-3-carboxylic acid methylamide. Yield: 99% of theory as a white solid; MS: m/e=379 (M+H)⁺.

EXAMPLE 11

(RS)-1-[4-(5-Fluoro-2-methyl-benzyloxy)-phenyl]-5-oxo-pyrrolidine-3-carboxylic acid methylamide The title compound is prepared by alkylation of the (RS)-1-(4-hydroxyphenyl)-5-oxo-pyrrolidine-3-carboxylic acid methyl ester with 5-fluoro-2-methylbenzyl bromide giving the (RS)-1-[4-(5-fluoro-2-methyl-benzyloxy)-phenyl]-5-oxo-pyrrolidine-3-carboxylic acid methyl ester as a white solid [71% of theory, MS: m/e=358 (M+H)⁺] which, thereupon, by treatment with methylamine in ethanol at 60° C. during 4 h yields the (RS)-1-[4-(5-fluoro-2-methyl-benzyloxy)-phenyl]-5-oxo-pyrrolidine-3-carboxylic acid methylamide. Yield: 53% of theory as a colorless solid. MS: m/e=357 (M+H)⁺.

EXAMPLE 12

(RS)-1-[4-(3-Methoxy-benzyloxy)-phenyl]-5-oxo-pyrrolidine-3-carboxylic acid methylamide In an analogous manner to that described in Example 1d) and e), starting from (RS)-1-(4-hydroxyphenyl)-5-oxo-pyrrolidine-3-carboxylic acid methyl ester [Example 1c)] the title compound is prepared by alkylation with 3-methoxy-benzyl bromide to obtain the (RS)-1-[4-(3-methoxy-benzyloxy)-phenyl]-5-oxo-pyrrolidine-3-carboxylic acid methyl ester as a yellowish oil and, thereupon, treatment with methylamine in ethanol at 80° C. during 18 h to yield the (RS)-1-[4-(3-methoxy-benzyloxy)-phenyl]-5-oxo-pyrrolidine-3-carboxylic acid methylamide. Yield: 75% of a colorless solid. MS: m/e=355 (M+H)⁺.

EXAMPLE 13

(RS)-1-[4-(2-Methoxy-benzyloxy)-phenyl]-5-oxo-pyrrolidine-3-carboxylic acid methylamide The title compound is prepared by alkylation of the (RS)-1-(4-hydroxyphenyl)-5-oxo-pyrrolidine-3-carboxylic acid methyl ester with 2-methoxybenzylbromide giving the (RS)-1-[4-(2-methoxy-benzyloxy)-phenyl]-5-oxo-pyrrolidine-3-carboxylic acid methyl ester as a light yellow oil [83% of theory, MS:m/e=355 (M+H)⁺ which, thereupon, by treatment with methylamine in ethanol at 80° C. yields the (RS)-1-[4-(2-methoxybenzyloxy)-phenyl]-5-oxo-pyrrolidine-3-carboxylic acid methylamide. Yield: 47% of theory as a white solid. MS: m/e=355 (M+H)⁺.

EXAMPLE 14

(RS)-5-Oxo-1-[4-(3-trifluoromethoxy-benzyloxy)-phenyl]-pyrrolidine-3-carboxylic acid methylamide The title compound is prepared by alkylation of the (RS)-1-(4-hydroxyphenyl)-5-oxo-pyrrolidine-3-carboxylic acid methyl ester with 3-trifluoromethoxybenzyl bromide giving the (RS)-5-oxo-1-[4-(3-trifluoromethoxy-benzyloxy)-phenyl]-pyrrolidine-3-carboxylic acid methyl ester as a white solid [40% of theory, MS: m/e=410 (M+H)⁺] which, thereupon, by treatment with methylamine in ethanol at 80° C. yields the (RS)-5-oxo-1-[4-(3-trifluoromethoxy-benzyloxy)-phenyl]-pyrrolidine-3-carboxylic acid methylamide. Yield: 59% of theory as a white powder. MS: m/e=409 (M+H)⁺.

EXAMPLE 15

(RS)-5-Oxo-1-[4-(3-trifluoromethyl-benzyloxy)-phenyl]-pyrrolidine-3-carboxylic acid methylamide In an analogous manner to that described in Example 1d) and e), starting from (RS)-1-(4-hydroxyphenyl)-5-oxo-pyrrolidine-3-carboxylic acid methyl ester [Example 1c)] the title compound is prepared by alkylation with 3-(trifluoromethyl)benzyl chloride to obtain the (RS)-5-oxo-1-[4-(3-trifluoromethyl-benzyloxy)-phenyl]-pyrrolidine-3-carboxylic acid methyl ester as a yellowish solid and, thereupon, treatment with methylamine in ethanol at 80° C. during 18 h to yield the (RS)-5-oxo-1-[4-(3-trifluoromethyl-benzyloxy)-phenyl]-pyrrolidine-3-carboxylic acid methylamide. Yield: 54% of a colorless solid. MS: m/e=393 (M+H)$^+$.

EXAMPLE 16

(RS)-1-[4-(3–Cyano-benzyloxy)-phenyl]-5-oxo-pyrrolidine-3-carboxylic acid methylamide The title compound is prepared by alkylation of the (RS)-1-(4-hydroxyphenyl)-5-oxo-pyrrolidine-3-carboxylic acid methyl ester with 3-cyanobenzyl bromide giving the (RS)-1-[4-(3-cyano-benzyloxy)-phenyl]-5-oxo-pyrrolidine-3-carboxylic acid methylester as a light yellow solid [69% of theory, MS: m/e=351 (M+H)$^+$] which, thereupon, by treatment with methylamine in ethanol at 80° C. yields the (RS)-1-[4-(3-cyano-benzyloxy)-phenyl]-5-oxo-pyrrolidine-3-carboxylic acid methylamide. Yield: 79% of theory as a white powder. MS: m/e=350 (M+H)$^+$.

EXAMPLE 17

(RS)-1-[4-(3-Fluoro-benzyloxy)-3-methyl-phenyl]-5-oxo-pyrrolidine-3-carboxylic acid methylamide a) (RS)-1-(4-Hydroxy-3-methyl-phenyl)-5-oxo-pyrrolidine-3-carboxylic acid

In an analogous manner to that described in Example 2a), 4-amino-o-cresol is reacted with itaconic acid at 140° C. during 10 min to yield the (RS)-1-(4-hydroxy-3-methyl-phenyl)-5-oxo-pyrrolidine-3-carboxylic acid as a light brown solid; MS: m/e=234 (M–H)+ which directly used in the next step.

b) (RS)-1-(4-Hydroxy-3-methyl-phenyl)-5-oxo-pyrrolidine-3-carboxylic acid methyl ester In analogy to the esterification described in Example 2b), the (RS)-1-(4-hydroxy-3-methyl-phenyl)-5-oxo-pyrrolidine-3-carboxylic acid is reacted with methanol in presence of sulfuric acid to yield the (RS)-1-(4-hydroxy-3-methyl-phenyl)-5-oxo-pyrrolidine-3-carboxylic acid methyl ester as a light brown solid; MS: m/e=250 (M+H)$^+$.

c) (RS)-1-[(4-(3-Fluoro-benzyloxy)-3-methyl-phenyl)-5-oxo-pyrrolidine-3-carboxylic acid methyl ester In analogy to the alkylation described in Example 1d), the (RS)-1-(4-hydroxy-3-methyl-phenyl)-5-oxo-pyrrolidine-3-carboxylic acid methyl ester is reacted with 3-fluorobenzyl bromide in presence of potassium carbonate in DMF at 80° C. to yield the (RS)-1-[(4-(3-fluoro-benzyloxy)-3-methyl-phenyl)-5-oxo-pyrrolidine-3-carboxylic acid methyl ester as a light brown oil; MS: m/e=375 (M+NH$_4$)$^+$.

d) (RS)-1-[(4-(3-Fluoro-benzyloxy)-3-methyl-phenyl)-5-oxo-pyrrolidine-3-carboxylic acid methyl Amide In analogy to the aminolysis described in Example 1e), the (RS)-1-[(4-(3-fluoro-benzyloxy)-3-methyl-phenyl)-5-oxo-pyrrolidine-3-carboxylic acid methyl ester is treated in a sealed tube with methylamine in ethanol at 60° C. for 18 h to yield the (RS)-1-[(4-(3-fluoro-benzyloxy)-3-methyl-phenyl)-5-oxo-pyrrolidine-3-carboxylic acid methyl amide as a light yellow solid; MS: m/e=357 (M+H)$^+$.

EXAMPLE 18

(RS)-1-[4-(4-Fluoro-benzyloxy)-3-methyl-phenyl]-5-oxo-pyrrolidine-3-carboxylic acid methylamide The title compound is prepared by alkylation of the (RS)-1-(4-hydroxy-3-methylphenyl)-5-oxo-pyrrolidine-3-carboxylic acid [Example 17b)] with 4-fluorobenzylbromide, in analogy to Example 1d), giving the (RS)-1-[4-(4-fluoro-benzyloxy)-3-methyl-phenyl]-5-oxo-pyrrolidine-3-carboxylic acid methylester as a light brown solid [26% of theory, MS: m/e=358 (M+H)$^+$] which, thereupon, by treatment with methylamine in ethanol at 80° C., in analogy to Example 1e), yields the (RS)-1-[4-(4-fluoro-benzyloxy)-3-methyl-phenyl]-5-oxo-pyrrolidine-3-carboxylic acid methylamide. Yield: 79% of theory as an off-white solid. MS: m/e=357 (M+H)$^+$.

EXAMPLE 19

(RS)-1-[4-(3–Chloro-benzyloxy)-3-methyl-phenyl]-5-oxo-pyrrolidine-3-carboxylic acid methylamide The title compound is prepared by alkylation of the (RS)-1-(4-hydroxy-3-methyl-phenyl)-5-oxo-pyrrolidine-3-carboxylic acid [Example 17b)] with 3-chlorobenzylchloride, in analogy to Example 1d), giving the (RS)-1-[4-(3-chloro-benzyloxy)-3-methyl-phenyl]-5-oxo-pyrrolidine-3-carboxylic acid methylester as a light brown oil [47% of theory, MS: m/e=374 (M+H)$^+$] which, thereupon, by treatment with methylamine in ethanol at 60° C., in analogy to Example 1e), yields the (RS)-1-[4-(3-chloro-benzyloxy)-3-methyl-phenyl]-5-oxo-pyrrolidine-3-carboxylic acid methylamide. Yield: 61% of theory as an white solid. MS: m/e=373 (M+H)$^+$.

EXAMPLE 20

(RS)-1-[3-Fluoro-4-(3-fluoro-benzyloxy)-phenyl]-5-oxo-pyrrolidine-3-carboxylic acid methylamide a) 2-Fluoro-1-(3-fluoro-benzyloxy)-4-nitro-benzene

A mixture of 10.0 g (63.7 mmol) 2-fluoro-4-nitrophenol, 17.6 g (127 mmol) potassium carbonate and 13.24 g (70.0 mmol) 3-fluorobenzyl bromide in 200 ml ethyl methyl ketone is hold overnight at 80° C. The reaction mixture is diluted with water and extracted with ethyl acetate. Crystallisation from diethyl ether/n-hexane gives 12.68 g (75%) of a slightly yellow solid. MS: m/e=265.1 (M+).

b) 3-Fluoro-4-(3-fluoro-benzyloxy)-phenylamine 12.68 g (47.8 mmol) 2-fluoro-1-(3-fluoro-benzyloxy)-4-nitro-benzene is dissolved in 150 ml ethyl acetate. 1.27 g platinum 5% on charcoal is added and the mixture is hydrogenated at RT and normal pressure for 6 hours. The catalyst is filtered off and the solution evaporated to yield 11.03 g (98%) of a dark brown liquid. MS: m/e=235.1 (M$^+$).

c) (RS)-1-[3-Fluoro-4-(3-fluoro-benzyloxy)-phenyl]-5-oxo-pyrrolidine-3-carboxylic acid The title compound is prepared in analogy to Example 1a) from 3-fluoro-4-(3-fluoro-benzyloxy)-phenylamine and itaconic acid. Yield: 86% of a colorless solid. MS: m/e=346.1 (M–H).

d) (RS)-1-[3-Fluoro-4-(3-fluoro-benzyloxy)-phenyl]-5-oxo-pyrrolidine-3-carboxylic acid methylamide 500 mg (1.44 mmol) (RS)-1-[3-fluoro-4-(3-fluoro-benzyloxy)-phenyl]-5-oxo-pyrrolidine-3-carboxylic acid is suspended in 5 ml dichloromethane. 0.52 ml (7.2 mmol) thionyl chloride is added and the reaction mixture hold at 40° C. overnight. The solvent is evaporated and the crude acid chloride is again dissolved in 5 ml dichloromethane. 0.76 ml (7.2 mmol) of a 33% solution of methylamine in ethanol is added and the mixture heated to 40° C. for 6 hours. Water is added and the product is extracted with ethyl acetate. Chromatography (silica gel, dichloromethane/methanol) yields 348 mg (67%) of a pink solid. MS: m/e=361.2 (M+H)$^+$.

EXAMPLE 21

(RS)-1-[2-Fluoro-4-(3-fluoro-benzyloxy)-phenyl]-5-oxo-pyrrolidine-3-carboxylic acid methylamide a) 2-Fluoro-4-(3-fluoro-benzyloxy)-1-nitro-benzene The title compound is prepared in analogy to Example 20a) from 3-fluoro-4-nitrophenol and 3-fluoro benzyl bromide. Yield: 100% of a colorless solid. MS: m/e=265.0 (M$^+$).

b) 2-Fluoro-4-(3-fluoro-benzyloxy)-phenylamine

The title compound is prepared in analogy to Example 20b) by hydrogenation of 2-fluoro-4-(3-fluoro-benzyloxy)-1-nitro-benzene. Yield: 98% of a dark brown liquid. MS: m/e=235.0 (M$^+$).

c) (RS)-1-[2-Fluoro-4-(3-fluoro-benzyloxy)-phenyl]-5-oxo-pyrrolidine-3-carboxylic acid The title compound is prepared in analogy to Example 20c) from 2-fluoro-4-(3-fluoro-benzyloxy)-phenylamine and itaconic acid. Yield: 67% of a purple solid. MS: m/e=346.1 (M+H)$^+$.

d) (RS)-1-[2-Fluoro-4-(3-fluoro-benzyloxy)-phenyl]-5-oxo-pyrrolidine-3-carboxylic acid methylamide The title compound is prepared in analogy to Example 20d) from (RS)-1-[2-fluoro-4-(3-fluoro-benzyloxy)-phenyl]-5-oxo-pyrrolidine-3-carboxylic acid and methylamine. Yield: 39% of a brownish solid. MS: m/e=361.2 (M+H)$^+$.

EXAMPLE 22

(RS)-1–12,5-Difluoro-4-(3-fluoro-benzyloxy)-phenyl]-5-oxo-pyrrolidine-3-carboxylic acid methylamide a) 1,4-Difluoro-2-(3-fluoro-benzyloxy)-5-nitro-benzene A mixture of 2.35 g (18.6 mmol) of 3-fluorobenzylalcohol and 0.55 g (1.7 mmol) of tris[2-(2-methoxyethoxy)ethyl] amine is treated portionwise under stirring with 1.06 g (18.6 mmol) of potassium hydroxide. Stirring is continued for 10 min if necessary under slight heating to reach a homogenous reaction mixture. Thereafter, 3.0 g (16.9 mmol) of 2,4,5-trifluoronitrobenzene are added dropwise. The reaction mixture becomes solid and is heated to 100° C. for 2 hours. For the working-up, the mixture is cooled to RT, then 25 ml water and 25 ml ethyl acetate are added and stirring continued for 30 min. The organic layer is separated and the aqueous layer is extracted twice with ethyl acetate. The combined organic layers are washed with water, then twice with 2N hydrochloric acid and finally with water. After drying over magnesium sulfate, the solution is evaporated under reduced pressure. During evaporation, the byproduct, 1-fluoro-2,4-bis-(3-fluorobenzyloxy)-5-nitro-benzene precipitates. For purification, the material obtained is chromatographed on silica gel using a 4:1-mixture of n-hexane and ethyl acetate as the eluent. There are obtained 2.63 g (55% of theory) of the 1,4-difluoro-2-(3-fluorobenzyloxy)-5-nitro-benzene as an off-white solid. MS: m/e=283 (M)$^+$.

b) 2,5-Difluoro-4-(3-fluoro-benzyloxy)-phenylamine

A solution of 2.63 g (9.3 mmol) of 1,4-difluoro-2-(3-fluoro-benzyloxy)-5-nitrobenzene in 25 ml of ethyl acetate is hydrogenated with Pt/C (5%) as the catalyst under normal pressure during 3 hours. For the working-up, the catalyst was filtered over a Dicalit layer and the solution evaporated under reduced pressure. There are obtained 2.25 g (95% of theory) of 2,5-difluoro-4-(3-fluoro-benzyloxy)-phenylamine as a brown solid; MS: m/e=253 (M)$^+$. The crude product is engaged in the next step without further purification.

c) (RS)-1-[2,5-Difluoro-4-(3-fluoro-benzyloxy)-phenyl]-5-oxo-pyrrolidine-3-carboxylic acid In an analogous manner to that described in Example 1a), 2,5-difluoro-4-(3-fluorobenzyloxy)-phenylamine was reacted with itaconic acid to yield (RS)-1-[2,5-difluoro-4-(3-fluoro-benzyloxy)-phenyl]-5-oxo-pyrrolidine-3-carboxylic acid (34.5% of theory) as a grey solid; MS: m/e=363 (M–H)$^+$.

d) (RS)-1-[2,5-Difluoro-4-(3-fluoro-benzyloxy)-phenyl]-5-oxo-pyrrolidine-3-carboxylic acid methylamide A solution of 365 mg (1.0 mmol) of (RS)-1-[2,5-difluoro-4-(3-fluoro-benzyloxy)-phenyl]-5-oxo-pyrrolidine-3-carboxylic acid is treated with 178 mg (1.1 mmol) of 1,1'-carbonyl-diimidazole, and the mixture is heated at 50° C. for 2 hours. Thereafter, the solution is cooled to RT and 47 mg (1.5 mmol) of methylamine (33% solution in ethanol) are added. After 18 hours the reaction is not complete, so that another 47 mg (1.5 mmol) of methylamine (33% solution in ethanol) are added and stirring is continued for 24 hours at 50° C. For the working-up, the reaction mixture is evaporated under reduced pressure. For purification, the material obtained is chromatographed on silica gel using a 95:5-mixture of dichloromethane and methanol as the eluent. There are obtained, after crystallization from ether, 136 mg (36% of theory) of the (RS)-1-[2,5-difluoro-4-(3-fluoro-benzyloxy)-phenyl]-5-oxo-pyrrolidine-3-carboxylic acid methylamide as an off-white solid. MS: m/e=379 (M+H)$^+$.

EXAMPLE 23

(RS)-1-(4-Benzyloxy-phenyl)-5-oxo-pyrrolidine-3-carboxylic acid methylamide

The title compound is prepared in analogy to Example 20d) from (RS)-1-(4-benzyloxy-phenyl)-5-oxo-pyrrolidine-3-carboxylic acid and methylamine. Yield: 73% of a slightly yellow solid. MS: m/e=325.4 (M+H)$^+$.

EXAMPLE 24

(R)-1-[4-(3-Fluoro-benzyloxy)-phenyl]-5-oxo-pyrrolidine-3-carboxylic acid methylamide a) (RS)-1-[4-(3-Fluoro-benzyloxy)-phenyl]-5-oxo-pyrrolidine-3-carboxylic acid 3.5 g (10.2 mmol) of [Rac] 1-[4-(3-fluoro-benzyloxy)-phenyl]-5-oxo-pyrrolidine-3-carboxylic acid methyl ester (Example 1d) are dispersed in 11.2 ml of a 1N solution of sodium hydroxide, and tetrahydrofuran is added to such an extent that a clear solution is obtained. Thereupon, the reaction mixture is heated to 50° C. during 1 h. For the working-up, the cooled solution is treated with 11.2 ml of 1N hydrochloric acid and THF evaporated under reduced pressure while the product starts to precipitate. The product is filtered and dried under vacuum to yield 2.39 g (71% of theory) of a white solid which is used in the next step without further purification.

b) (RS)-1-[4-(3-Fluoro-benzyloxy)-phenyl]-5-oxo-pyrrolidine-(3RS)-carbonyl Chloride A dispersion of 2.37 g (7.2 mmol) of (RS)-1-[4-(3-fluoro-benzyloxy)-phenyl]-5-oxo-pyrrolidine-3-carboxylic acid in 50 ml of dichloromethane is treated with 3.1 ml (43.2 mmol) of thionylchloride at RT during 18 h. For the working-up, the reaction mixture is evaporated under reduced pressure to dryness, then the residue is dispersed in toluene and evaporated to dryness again to yield quantitatively the acid chloride as a yellowish solid which is used in the next step without further purification.

c) (3RS)-1-[4-(3-Fluoro-benzyloxy)-phenyl]-5-oxo-pyrrolidine-3-carboxylic acid (1R)-phenyl-ethyl ester A solution of 2.49 g (7.2 mmol) of (RS)-1-[4-(3-fluoro-benzyloxy)-phenyl]-5-oxo-pyrrolidine-(3RS)-carbonyl chloride in 42 ml of dichloromethane is prepared and cooled to 0° C. The solution of 0.73 g (6.0 mmol) of (R)-(+)-1-phenylethanol in a mixture of 10 ml of dichloromethane and 0.48 ml pyridine is added dropwise. After complete addition, the reaction mixture is warmed to RT and stirring continued for 20 min. For the working-up, the reaction mixture is evaporated under reduced pressure and 3.84 g of a yellowish solid residue are obtained. For purification, the material obtained is chromatographed on silica gel by flas-chromatography using a gradient of n-hexane to a 4:1 mixture of n-hexane and ethyl acetate as the eluent. There are obtained 1.96 g (76% of theory) of the mixture of the two diastereomers as a white solid. MS: m/e=434 (M+H)$^+$.

d) (3R)-1-[4-(3-Fluoro-benzyloxy)-phenyl]-5-oxo-pyrrolidine-3-carboxylic acid (1R)-phenyl-ethyl ester and (3S)-1-[4-(3-fluoro-benzyloxy)-phenyl]-5-oxo-pyrrolidine-3-carboxylic acid (1R)-phenyl-ethyl ester The separation of 1.80 g (4.2 mmol) of the two isomers (Example 24c) is performed on a preparative chiral HPLC column (CHIRALPAK® AD, pressure: 17 bar, flow: 35 ml/min) using a 4:1 mixture of n-heptane and ethanol as the eluent. There are obtained 763 mg (42.4% of theory) of the first eluting isomer (3R)-1-[4-(3-fluoro-benzyloxy)-phenyl]-5-oxo-pyrrolidine-3-carboxylic acid (1R)-phenyl-ethyl ester [MS: m/e=434 (M$^+$+H)] and 860 mg (47.8% of theory) of the later eluting isomer (3S)-1-[4-(3-fluoro-benzyloxy)-phenyl]-5-oxo-pyrrolidine-3-carboxylic acid (1R)-phenyl-ethyl ester [MS: m/e=434 (M+H)$^+$], each as a white solid.

e) (R)-1-[4-(3-Fluoro-benzyloxy)-phenyl]-5-oxo-pyrrolidine-3-carboxylic acid

A solution of 0.622 g (1.44 mmol) of (3R)-1-[4-(3-fluoro-benzyloxy)-phenyl]-5-oxo-pyrrolidine-3-carboxylic acid (1R)-phenyl-ethyl ester in 17 ml of dioxane is treated with 1.68 ml of hydrochloric acid (37%) and the mixture is heated to 50° C. during 18 h. For the work-up, the reaction mixture is evaporated under reduced pressure and the yellowish residue obtained is triturated with ethyl acetate at −10° C. The mixture is filtered and the white solid dried under vacuum to yield 344 mg (73% of theory) of the (R)-acid which is used in the next step without further purification. MS: m/e=328 (M−H)$^+$.

f) (R)-1-[4-(3-Fluoro-benzyloxy)-phenyl]-5-oxo-pyrrolidine-3-carboxylic acid methylamide A solution of 0.339 g (1.03 mmol) of (S)-1-[4-(3-fluoro-benzyloxy)-phenyl]-5-oxo-pyrrolidine-3-carboxylic acid in 21 ml of N,N-dimethylformamide, cooled to 0° C., is treated consecutively with 0.15 ml (1.13 mmol) of triethylamine, 0.390 g (1.03 mmol) of HBTU, 0.085 g (1.24 mmol) of methylamine hydrochloride, and 0.15 ml (1.13 mmol) of triethylamine. The reaction is stopped after 30 min and the orange colored solution is evaporated under reduced pressure. The residue obtained is triturated in ethyl acetate, the white solid product is filtered, thereafter dissolved in dichloromethane and the solution washed three times with water. The organic phase is dried over sodium sulfate, then evaporated under reduced pressure to yield 231 mg (66% of theory) of a white solid. MS: m/e=343 (M+H)$^+$; $[\alpha]_{589}$=−25.48° (c=0.954, CH$_2$Cl$_2$).

EXAMPLE 25

(S)-1-[4-(3-Fluoro-benzyloxy)-phenyl]-5-oxo-pyrrolidine-3-carboxylic acid methylamide a) (S)-1-[4-(3-Fluoro-benzyloxy)-phenyl]-5-oxo-pyrrolidine-3-carboxylic acid In an analogous manner to that described in Example 24e), starting from (3S)-1-[4-(3-fluoro-benzyloxy)-phenyl]-5-oxo-pyrrolidine-3-carboxylic acid (1R)-phenyl-ethyl ester (Example 24d) by acidic hydrolysis of the ester there is obtained (S)-1-[4-(3-fluoro-benzyl-oxy)-phenyl]-5-oxo-pyrrolidine-3-carboxylic acid as a white solid which is used in the next step without further purification. MS: m/e=328 (M−H)$^+$.

b) (S)-1-[4-(3-Fluoro-benzyloxy)-phenyl]-5-oxo-pyrrolidine-3-carboxylic acid methylamide In an analogous manner to that described in Example 24f), by condensing (S)-1-[4-(3-fluoro-benzyloxy)-phenyl]-5-oxo-pyrrolidine-3-carboxylic acid with methylamine using HBTU as the condensation agent there is obtained (S)-1-[4-(3-fluoro-benzyloxy)-phenyl]-5-oxo-pyrrolidine-3-carboxylic acid methylamide as a white solid. MS: m/e=343 (M+H)$^+$; $[\alpha]_{589}$=+28.17° (c=0.831, CH$_2$Cl$_2$).

EXAMPLE 26

(R)-1-(4-Benzyloxy-phenyl)-5-oxo-pyrrolidine-3-carboxylic acid methylamide a) (RS)-1-(4-Benzyloxy-phenyl)-5-oxo-pyrrolidine-3-carbonyl Chloride

In an analogous manner to that described in Example 24b), starting from (RS)-1-(4-benzyloxy-phenyl)-5-oxo-pyrrolidine-3-carboxylic acid (Example 1a) by treatment with thionylchloride there is obtained (RS)-1-(4-benzyloxy-phenyl)-5-oxo-pyrrolidine-3-carbonyl chloride as a yellowish solid which is directly used in the next step without further purification.

b) (3R)-1-(4-benzyloxy-phenyl)-5-oxo-pyrrolidine-3-carboxylic acid (1R)-phenyl-ethyl ester and (3S)-1-(4-benzyloxy-phenyl)-5-oxo-pyrrolidine-3-carboxylic acid (1R)-phenyl-ethyl ester In an analogous manner to that described in Example 24c) and 24d), starting from (RS)-1-(4-benzyloxy-phenyl)-5-oxo-pyrrolidine-3-carbonyl chloride by reaction with (R)-(+)-1-phenylethanol there is obtained the mixture of the two isomers (3RS)-1-(4-benzyl-oxy-phenyl)-5-oxo-pyrrolidine-3-carboxylic acid (1R)-phenyl-ethyl ester which is separated on a preparative chiral HLPC column (conditions see Example 24d) to yield the first eluting (3R)-1-(4-benzyloxy-phenyl)-5-oxo-pyrrolidine-3-carboxylic acid (1R)-phenyl-ethyl ester [MS: m/e=416 (M$^+$+H)] and (3S)-1-(4-benzyloxy-phenyl)-5-oxo-pyrrolidine-3-carboxylic acid (1R)-phenyl-ethyl ester [MS: m/e=416 (M+H)$^+$] as a white solid each.

c) (3R)-1-(4-Benzyloxy-phenyl)-5-oxo-pyrrolidine-3-carboxylic acid

In an analogous manner to that described in Example 24e), starting from (3R)-1-(4-benzyloxy-phenyl)-5-oxo-pyrrolidine-3-carboxylic acid (1R)-phenyl-ethyl ester by acidic hydrolysis of the ester there is obtained (3R)-1-(4-benzyloxy-phenyl)-5-oxo-pyrrolidine-3-carboxylic acid as a white solid which is used in the next step without further purification. MS: m/e=310 (M−H)$^+$.

d) (R)-1-(4-Benzyloxy-phenyl)-5-oxo-pyrrolidine-3-carboxylic acid methylamide In an analogous manner to that described in Example 24f), by condensing (R)-1-(4-benzyloxy-phenyl)-5-oxo-pyrrolidine-3-carboxylic acid with methylamine using HBTU as the condensation agent there is obtained (R)-1-(4-benzyloxy-phenyl)-5-oxo-pyrrolidine-3-carboxylic acid methylamide as a white solid. MS: m/e=325 (M+H)$^+$; $[\alpha]_{589}$=−27.550 (c=0.958, CH$_2$Cl$_2$).

EXAMPLE 27

(S)-1-(4-Benzyloxy-phenyl)-5-oxo-pyrrolidine-3-carboxylic acid methylamide a) (RS)-1-(4-Benzyloxy-phenyl)-5-oxo-pyrrolidine-3-carbonyl Chloride

In an analogous manner to that described in Example 24b), starting from (RS)-1-(4-benzyloxy-phenyl)-5-oxo-pyrrolidine-3-carboxylic acid (Example 1a) by treatment with thionylchloride there is obtained (RS)-1-(4-benzyloxy-phenyl)-5-oxo-pyrrolidine-3-carbonyl chloride as a yellowish solid which is directly used in the next step without further purification.

b) (3R)-1-(4-benzyloxy-phenyl)-5-oxo-pyrrolidine-3-carboxylic acid (1R)-phenyl-ethyl ester and (3S)-1-(4-benzyloxy-phenyl)-5-oxo-pyrrolidine-3-carboxylic acid (1R)-phenyl-ethyl ester In an analogous manner to that described in Example 24c and 24d, starting from (RS)-1-(4-benzyloxy-phenyl)-5-oxo-pyrrolidine-3-carbonyl chloride by reaction with (R)-(+)-1-phenylethanol there is obtained the mixture of the two isomers (3RS)-1-(4-benzyloxy-phenyl)-5-oxo-pyrrolidine-3-carboxylic acid (1R)-phenyl-ethyl ester which is separated on a preparative chiral HLPC column (CHIRALPAK® AD, pressure: 17 bar, flow: 35 ml/min) using a 4:1 mixture of n-heptane and isopropanol as the eluent) to yield the first eluting (3R)-1-(4-benzyloxy-phenyl)-5-oxo-pyrrolidine-3-carboxylic acid (1R)-phenyl-ethyl ester [MS: m/e=416 (M$^+$+H)] and (3S)-1-(4-benzyloxy-phenyl)-5-oxo-pyrrolidine-3-carboxylic acid (1R)-phenyl-ethyl ester [MS: m/e=416 (M+H)$^+$] as a white solid each.

c) (S)-1-(4-Benzyloxy-phenyl)-5-oxo-pyrrolidine-3-carboxylic acid

In an analogous manner to that described in Example 24e, starting from (3S)-1-(4-benzyloxy-phenyl)-5-oxo-pyrrolidine-3-carboxylic acid (1R)-phenyl-ethyl ester by acidic hydrolysis of the ester there is obtained (3S)-1-(4-benzyloxy-phenyl)-5-oxo-pyrrolidine-3-carboxylic acid as a white solid which is used in the next step without further purification. MS: m/e=310 (M−H)⁺.

d) (S)-1-(4-Benzyloxy)-phenyl)-5-oxo-pyrrolidine-3-carboxylic acid methylamide In an analogous manner to that described in Example 24f, by condensing (S)-1-(4-benzyloxy)-phenyl)-5-oxo-pyrrolidine-3-carboxylic acid with methylamine using HBTU as the condensation agent there is obtained (S)-1-(4-benzyloxy)-phenyl)-5-oxo-pyrrolidine-3-carboxylic acid methylamide as a white solid. MS: m/e=325 (M+H)⁺; $[\alpha]_{589}$=+32.02° (c=1.037, $CH_2Cl_2$).

EXAMPLE 28

(R)-1-[4-(4-Fluoro-benzyloxy)-phenyl]-5-oxo-pyrrolidine-3-carboxylic acid methylamide a) (R)-1-(4-Hydroxy-phenyl)-5-oxo-pyrrolidine-3-carboxylic acid methyl ester A suspension of 2.51 g (10.6 mmol) of (RS)-1-(4-hydroxy-phenyl)-5-oxo-pyrrolidine-3-carboxylic acid methyl ester in 10 ml of phosphate buffer [c($KH_2PO_4$)=0.05 mol/l], 25 ml of sodium sulfate solution [c($Na_2SO_4$)=4 mol/l], 45 ml of deionised water, and 20 ml of tert-butylmethylether is adjusted to pH 6.0. Under moderate stirring, 51.3 mg of cholesterase from *Candida cylindracea* (Roche Applied Science, Industrial Products, Enzyme Projects, Sandhofer Str. 116, D-68305 Mannheim, Germany, order no. 10129046103) are added in solid form. By an automatic pH-Stat-System, the pH is kept constant at 6.0 by addition of sodium hydroxide solution [c(NaOH)=1.0 mol/l] at RT. The progress of the reaction is followed by the consumption of sodium hydroxide solution. After the addition of 5.21 ml of sodium hydroxide solution, the reaction is stopped by addition of dichloromethane. The organic layer is separated, then washed three times with water, thereafter, dried over sodium sulfate, and finally evaporated. The crude ester is a slightly rose oil which after trituration in tert-butylmethylether at RT is obtained as a white solid. The product is collected on a filter funnel and yields after drying under high vacuum at RT 1.11 g (44.3% of theory) of (R)-1-(4-hydroxy-phenyl)-5-oxo-pyrrolidine-3-carboxylic acid methyl ester; m.p.: 122.9° C.; optical integrity: 97.9% e.e.; $[\alpha]^{20}_D$=−35.2 (c=1.162 g/100 ml $CHCl_3$).

b) (R)-1-[4-(4-Fluoro-benzyloxy)-phenyl]-5-oxo-pyrrolidine-3-carboxylic acid methyl ester A solution of 550 mg (4.3 mmol) of 4-fluoro-benzylalcohol and 1.27 g (4.7 mmol) of triphenylphosphine in 7 ml of tetrahydrofurane is added dropwise at 0° C. to a solution of 1.11 g (4.7 mmol) of (R)-1-(4-hydroxy-phenyl)-5-oxo-pyrrolidine-3-carboxylic acid methyl ester and 1.01 g (4.7 mmol) of diisopropyl azodicarboxylate in 11 ml of tetrahydrofurane. The mixture is left to warm to RT and stirring is continued for 18 hours. For the working-up, after addition of 2 g of silica gel the reaction mixture is evaporated under reduced pressure. For purification, the material obtained is chromatographed on silica gel using first a 2:1-mixture, then a 1:1-mixture of heptane and ethyl acetate as the eluent. There are obtained 1.39 g (95% of theory) of (R)-1-[4-(4-fluoro-benzyloxy)-phenyl]-5-oxo-pyrrolidine-3-carboxylic acid methyl ester as a white solid; MS: m/e=344 (M+H)⁺.

c) (R)-1-[4-(4-Fluoro-benzyloxy)-phenyl]-5-oxo-pyrrolidine-3-carboxylic acid A solution of 1.27 g (3.7 mmol) of (R)-1-[4-(4-fluoro-benzyloxy)-phenyl]-5-oxo-pyrrolidine-3-carboxylic acid methyl ester in 77 ml of dioxane is treated with 8.64 ml of hydrochloric acid (37%). The mixture is heated at 52° C. for 18 h in a closed flask. For the working-up, the solution is evaporated under reduced pressure to yield the crude acid as a yellowish solid. For purification, the crude acid is triturated at −5° C. in 10 ml of ethyl acetate. The solid is collected on a filter funnel and then dried under high vacuum to yield 0.624 g (51% of theory) of (R)-1-[4-(4-fluoro-benzyloxy)-phenyl]-5-oxo-pyrrolidine-3-carboxylic acid as a white solid; MS: m/e=330 (M+H)⁺.

d) (R)-1-[4-(4-Fluoro-benzyloxy)-phenyl]-5-oxo-pyrrolidine-3-carboxylic acid methylamide In an analogous manner to that described in Example 24 f), by condensing the (R)-1-[4-(4-fluoro-benzyloxy)-phenyl]-5-oxo-pyrrolidine-3-carboxylic acid with methylamine using HBTU as the condensation agent the (R)-1-[4-(4-fluoro-benzyloxy)-phenyl]-5-oxo-pyrrolidine-3-carboxylic acid methylamide is obtained as a white solid. MS: m/e=343 (M+H)⁺.

EXAMPLE 29

(R)-1-[4-(3-Fluoro-benzyloxy)-phenyl]-5-oxo-pyrrolidine-3-carboxylic acid methylamide (cf. Example 24)

a) (R)-1-[4-(3-Fluoro-benzyloxy)-phenyl]-5-oxo-pyrrolidine-3-carboxylic acid methyl ester In an analogous manner to that described in Example 28b), the alkylation of the (R)-1-(4-hydroxy-phenyl)-5-oxo-pyrrolidine-3-carboxylic acid methyl ester [Example 28 a)] with 3-fluorobenzylalcohol yields the (R)-1-[4-(3-fluoro-benzyloxy)-phenyl]-5-oxo-pyrrolidine-3-carboxylic acid methyl ester as a white solid. MS: m/e=344 (M+H)⁺.

b) (R)-1-[4-(3-Fluoro-benzyloxy)-phenyl]-5-oxo-pyrrolidine-3-carboxylic acid In an analogous manner to that described in Example 28c), the acidic hydrolysis of the (R)-1-[4-(3-fluoro-benzyloxy)-phenyl]-5-oxo-pyrrolidine-3-carboxylic acid methyl ester yields the (R)-1-[4-(3-fluoro-benzyloxy)-phenyl]-5-oxo-pyrrolidine-3-carboxylic acid as a white solid. MS: m/e=328 (M+H)⁺.

c) (R)-1-[4-(3-Fluoro-benzyloxy)-phenyl]-5-oxo-pyrrolidine-3-carboxylic acid methylamide In an analogous manner to that described in Example 24 f), the condensation of the (R)-1-[4-(3-fluoro-benzyloxy)-phenyl]-5-oxo-pyrrolidine-3-carboxylic acid with methylamine using HBTU as the condensation agent yields the (R)-1-[4-(3-fluoro-benzyloxy)-phenyl]-5-oxo-pyrrolidine-3-carboxylic acid methylamide as a white solid. MS: m/e=343 (M+H)⁺.

EXAMPLE 30

(R)-1-[4-(3–Chloro-benzyloxy)-phenyl]-5-oxo-pyrrolidine-3-carboxylic acid methylamide a) ®-1-[4-(3–Chloro-benzyloxy)-phenyl]-5-oxo-pyrrolidine-3-carboxylic acid methyl ester In an analogous manner to that described in Example 28b), the alkylation of the ®-1-(4-hydroxy-phenyl)-5-oxo-pyrrolidine-3-carboxylic acid methyl ester [Example 28 a)] with 3-chlorobenzylalcohol yields the (R)-1'-[4-(3-chloro-benzyloxy)-phenyl]-5-oxo-pyrrolidine-3-carboxylic acid methyl ester as a white solid. MS: m/e=360 (M+H)$^+$.

b) (R)-1-[4-(3–Chloro-benzyloxy)-phenyl]-5-oxo-pyrrolidine-3-carboxylic acid In an analogous manner to that described in Example 28c), the acidic hydrolysis of the (R)-1-[4-(3-chloro-benzyloxy)-phenyl]-5-oxo-pyrrolidine-3-carboxylic acid methyl ester yields the (R)-1-[4-(3-chloro-benzyloxy)-phenyl]-5-oxo-pyrrolidine-3-carboxylic acid as a white solid. MS: m/e=344 (M+H)$^+$.

c) (R)-1-[4-(3–Chloro-benzyloxy)-phenyl]-5-oxo-pyrrolidine-3-carboxylic acid methylamide In an analogous manner to that described in Example 24f), the condensation of the (R)-1-[4-(3-chloro-benzyloxy)-phenyl]-5-oxo-pyrrolidine-3-carboxylic acid with methylamine using HBTU as the condensation agent yields the (R)-1-[4-(3-chloro-benzyloxy)-phenyl]-5-oxo-pyrrolidine-3-carboxylic acid methylamide as a white solid. MS: m/e=359 (M+H)$^+$.

EXAMPLE 31

(R)-1-[4-(2,6-Difluoro-benzyloxy)-phenyl]-5-oxo-pyrrolidine-3-carboxylic acid methylamide a) (R)-1-[4-(2,6-Difluoro-benzyloxy)-phenyl]-5-oxo-pyrrolidine-3-carboxylic acid methyl ester In an analogous manner to that described in Example 28b), the alkylation of the (R)-1-(4-hydroxy-phenyl)-5-oxo-pyrrolidine-3-carboxylic acid methyl ester [Example 28a)] with 2,6-difluorobenzylalcohol yields the (R)-1-[4-(2,6-difluoro-benzyloxy)-phenyl]-5-oxo-pyrrolidine-3-carboxylic acid methyl ester as a white solid. MS: m/e=362 (M+H)$^+$.

b) (R)-1-[4-(2,6-Difluoro-benzyloxy)-phenyl]-5-oxo-pyrrolidine-3-carboxylic acid In an analogous manner to that described in Example 28c), the acidic hydrolysis of the (R)-1-[4-(2,6-difluoro-benzyloxy)-phenyl]-5-oxo-pyrrolidine-3-carboxylic acid methyl ester yields the (R)-1-[4-(2,6-difluoro-benzyloxy)-phenyl]-5-oxo-pyrrolidine-3-carboxylic acid as a white solid. MS: m/e=346 (M+H)$^+$.

c) (R)-1-[4-(2,6-Difluoro-benzyloxy)-phenyl]-5-oxo-pyrrolidine-3-carboxylic acid methylamide In an analogous manner to that described in Example 24f), the condensation of the (R)-1-[4-(2,6-difluoro-benzyloxy)-phenyl]-5-oxo-pyrrolidine-3-carboxylic acid with methylamine using HBTU as the condensation agent yields the (R)-1-[4-(2,6-difluoro-benzyloxy)-phenyl]-5-oxo-pyrrolidine-3-carboxylic acid methylamide as a white solid. MS: m/e=361 (M+H)$^+$.

EXAMPLE 32

(R)-5-Oxo-1-[4-(2,4,6-trifluoro-benzyloxy)-phenyl]-pyrrolidine-3-carboxylic acid methylamide a) (R)-5-Oxo-1-[4-(2,4,6-Trifluoro-benzyloxy)-phenyl]-pyrrolidine-3-carboxylic acid methyl ester In an analogous manner to that described in Example 28b), the alkylation of the (R)-1-(4-hydroxy-phenyl)-5-oxo-pyrrolidine-3-carboxylic acid methyl ester [Example 28a)] with 2,4,6-trifluorobenzylalcohol yields the (R)-5-oxo-1-[4-(2,4,6-trifluoro-benzyloxy)-phenyl]-pyrrolidine-3-carboxylic acid methyl ester as a white solid. MS: m/e=380 (M+H)$^+$.

b) (R)-5-Oxo-1-[4-(2,4,6-Trifluoro-benzyloxy)-phenyl]-pyrrolidine-3-carboxylic acid In an analogous manner to that described in Example 28 c), the acidic hydrolysis of the (R)-5-oxo-1-[4-(2,4,6-trifluoro-benzyloxy)-phenyl]-pyrrolidine-3-carboxylic acid methyl ester yields the (R)-5-oxo-1-[4-(2,4,6-trifluoro-benzyloxy)-phenyl]-pyrrolidine-3-carboxylic acid as a white solid. MS: m/e=364 (M+H)$^+$.

c) (R)-5-Oxo-1-[4-(2,4,6-Trifluoro-benzyloxy)-phenyl]-pyrrolidine-3-carboxylic acid methylamide In an analogous manner to that described in Example 24 f), the condensation of the (R)-5-oxo-1-[4-(2,4,6-trifluoro-benzyloxy)-phenyl]-pyrrolidine-3-carboxylic acid with methylamine using HBTU as the condensation agent yields the (R)-5-Oxo-1-[4-(2,4,6-Trifluoro-benzyloxy)-phenyl]-pyrrolidine-3-carboxylic acid methylamide as a white solid. MS: m/e=379 (M+H)$^+$.

EXAMPLE 33

(RS)-1-[4-(3,4-Difluoro-benzyloxy)-phenyl]-5-oxo-pyrrolidin-3-yl}-acetonitrile a) (RS)-1-[4-(3,4-Difluoro-benzyloxy)-phenyl]-4-hydroxymethyl-pyrrolidin-2-one 2.0 g (5.54 mmol) (RS)-1-[4-(3,4-Difluoro-benzyloxy)-phenyl]-5-oxo-pyrrolidine-3-carboxylic acid methyl ester is dissolved in 50 ml THF. 1.05 g (27.7 mmol) of sodium borohydride is added and the reaction mixture boiled under reflux for 24 hours. Water is added and the product is extracted with ethyl acetate to yield 1.68 g (91%) of a yellowish solid. MS: m/e=334.3 (M+H)$^+$.

b) (RS)-1-[4-(3,4-Difluoro-benzyloxy)-phenyl]-5-oxo-pyrrolidin-3-yl}-acetonitrile 300 mg (0.9 mmol) (RS)-1-[4-(3,4-Difluoro-benzyloxy)-phenyl]-4-hydroxymethyl-pyrrolidin-2-one and 0.136 mg (1.35 mmol) triethylamine are dissolved in 20 ml dichloromethane and cooled to 0° C. 155 mg (1.35 mmol) methanesulfonyl chloride is added. The mixture is stirred at 0° C. for 30 min then at RT for 3 hours, then washed successively with water, 1 M hydrochloric acid, 10% sodium hydrogen carbonate and saturated sodium chloride solution. Drying and evaporation gives the crude mesylate, which is dissolved in 2 ml N,N-dimethylformamide. 110 mg (2.25 mmol) sodium cyanide is added and the reaction mixture is hold at 100° C. for 24 hours. Hydrolysis and extraction with ethyl acetate gives the crude nitrile, which is subjected to chromatography (silica gel, dichloromethane/methanol). Yield: 20% of a brownish solid. MS: m/e=343.1 (M+H)$^+$.

EXAMPLE 34

(RS)-{1-[4-(3-Fluoro-benzyloxy)-phenyl]-5-oxo-pyrrolidin-3-yl}-acetonitrile a) (RS)-1-[4-(3-Fluoro-benzyloxy)-phenyl]-4-hydroxymethyl-pyrrolidin-2-one The title compound is prepared in analogy to Example 33a) from (RS)-1-[4-(3-fluoro-benzyloxy)-phenyl]-5-oxo-pyrrolidine-3-carboxylic acid methyl ester and sodium borohydride. Yield: 82% of a colorless solid. MS: m/e=316.3 (M+H)$^+$.

b) (RS)-{1-[4-(3-Fluoro-benzyloxy)-phenyl]-5-oxo-pyrrolidin-3-yl}-acetonitrile

The title compound is prepared in analogy to Example 33b) from (RS)-1-[4-(3-fluoro-benzyloxy)-phenyl]-4-hydroxymethyl-pyrrolidin-2-one, methanesulfonyl chloride and sodium cyanide. Yield: 27% of a colorless solid. MS: m/e=325.2 (M+H)$^+$.

EXAMPLE 35

(RS)-[1-(4-Benzyloxy-phenyl)-5-oxo-pyrrolidin-3-yl]-acetonitrile a) (RS)-1-(4-Benzyloxy-phenyl)-4-hydroxymethyl-pyrrolidin-2-one The title compound is prepared in analogy to Example 33a) from (RS)-1-(4-benzyloxy-phenyl)-5-oxo-pyrrolidine-3-carboxylic acid methyl ester and sodium borohydride. Yield: 82% of a colorless solid. MS: m/e=298.3 (M+H)$^+$.

b) (RS)-1-(4-Benzyloxy-phenyl)-4-chloromethyl-pyrrolidin-2-one 740 mg (2.49 mmol) (RS)-1-(4-benzyloxy-phenyl)-4-hydroxymethyl-pyrrolidin-2-one is dissolved in 20 ml toluene. 1.08 ml (14.9 mmol) thionyl chloride is added and the mixture refluxed for 6 hours. Evaporation and chromatography (silica gel, n-hexane/ethyl acetate 1:1) yields 123 mg (16%) of a brownish semisolid. MS: m/e=315.2 (M+).

c) (RS)-[1-(4-Benzyloxy-phenyl)-5-oxo-pyrrolidin-3-yl]-acetonitrile 123 mg (0.39 mmol) (RS)-1-(4-benzyloxy-phenyl)-4-chloromethyl-pyrrolidin-2-one is dissolved in 2.5 ml N,N-dimethylformamide. After addition of 29 mg (0.58 mmol) sodium cyanide and 6 mg (0.04 mmol) sodium iodide, the mixture is hold at 120° C. for 15 min. Dilution with water and extraction with ethyl acetate yields 44 mg (37%) of a brownish solid. MS: m/e=307.3 (M+H)$^+$.

EXAMPLE 36

(RS)-(E)-1-{4-[2-(3-Fluoro-phenyl)-vinyl]-phenyl}-5-oxo-pyrrolidine-3-carboxylic acid methylamide a) (E)-1-Fluoro-3-[2-(4-nitrophenyl)ethenyl]-benzene A suspension of 677 mg of sodium hydride (55% dispersion in oil) in 10 ml of N,N-dimethylformamide are cooled to 0° C. Thereupon, 5.61 g (20.5 mmol) of diethyl (4-nitro-benzyl)phosphonate are added portionwise. The reaction mixture is left to warm to RT and stirred for 1.5 hours. Thereafter, the mixture is cooled to −10° C. and a solution of 1.5 g (12.1 mmol) of 3-fluorobenzaldehyde in 5 ml N,N-dimethylformamide is added dropwise. Stirring is continued for 30 min at 0° C., then at RT. For the working-up, ice and ethyl acetate is added to the reaction mixture. The organic layer is separated, dried over magnesium sulfate and evaporated under reduced pressure to yield the crude crystalline product, which after recrystallisation from a mixture of ether and heptane gives 2.41 g (82% of theory) of (E)-1-fluoro-3-[2-(4-nitrophenyl)ethenyl]-benzene as a yellow solid; MS: m/e=243(M)$^+$.

b) (E)-4-[2-(3-Fluoro-phenyl)-vinyl]-phenylamine

A solution of 2.41 g (10 mmol) (E)-1-fluoro-3-[2-(4-nitrophenyl)ethenyl]-benzene in 25 ml of ethyl acetate is flushed with argon and, thereafter, hydrogenated at RT and atmospheric pressure during 4 hours using 0.241 g of platinum on carbon (5%) as the catalyst. For the working-up, the catalyst is filtered over Dicalit and the resulting solution is evaporated under reduced pressure. The solid material obtained is crystallised from a mixture of ether and heptane to yield 1.32 g (62.5% of theory) of (E)-4-[2-(3-fluoro-phenyl)-vinyl]-phenylamine as an orange solid; MS: m/e=213 (M)$^+$.

c) (RS)-(E)-1-{4-[2-(3-Fluoro-phenyl)-vinyl]-phenyl}-5-oxo-pyrrolidine-3-carboxylic acid A mixture of 600 mg (2.8 mmol) of (E)-4-[2-(3-fluoro-phenyl)-vinyl]-phenylamine and 366 mg (2.8 mmol) of itaconic acid is heated to 130° C. After 1 hour, the molten material is cooled to RT and, thereafter, the resulting solid is triturated with ethyl acetate to yield 568 mg (62% of theory) of (RS)-(E)-1-{4-[2-(3-fluoro-phenyl)-vinyl]-phenyl}-5-oxo-pyrrolidine-3-carboxylic acid as a fine yellow powder; MS: m/e=324 (M−H)$^+$.

d) (RS)-(E)-1-{4-[2-(3-Fluoro-phenyl)-vinyl]-phenyl}-5-oxo-pyrrolidine-3-carboxylic acid methylamide A suspension of 300 mg (0.92 mmol) of (E)-1-{4-[2-(3-fluoro-phenyl)-vinyl]-phenyl}-5-oxo-pyrrolidine-3-carboxylic acid in 5 ml of dichloromethane is treated with 549 mg (4.6 mmol) of thionylchloride and heated to 45° C. for 18 hours. Thereafter, the reaction mixture is evaporated to dryness under reduced pressure. The crude acid chloride obtained is dissolved in 5 ml of dry dichloromethane, then, at RT, 0.58 ml (4.61 mmol) of a solution of methylamine in ethanol (33%) is added and stirring continued for 3 hours. For the working-up, the reaction mixture is treated with water and dichloromethane. The organic layer is separated, dried over magnesium sulfate and evaporated. For purification, the crude product is chromatographed on silica gel using a 95:5-mixture of dichloromethane and methanol as the eluent. After crystallization from a mixture of dichloromethane and ether, there are obtained 207 mg (66% of theory) of (RS)-(E)-1-{4-[2-(3-fluoro-phenyl)-vinyl]-phenyl}-5-oxo-pyrrolidine-3-carboxylic acid methylamide as a light brown solid; MS: m/e=339 (M+H)+.

EXAMPLE 37

(RS)-(E)-1-{4-[2-(4-Methoxy-phenyl)-vinyl]-phenyl}-5-oxo-pyrrolidine-3-carboxylic acid methylamide a) (E)-1-Methoxy-4-[2-(4-nitrophenyl)ethenyl]-benzene In an analogous manner to that described in Example 36a), the reaction of diethyl (4-nitrobenzyl)phosphonate with 4-methoxybenzaldehyde yields the (E)-1-methoxy-4-[2-(4-nitrophenyl)ethenyl]-benzene as a yellow solid; MS: m/e=255 (M+H)+.

b) (E)-4-[2-(4-Methoxy-phenyl)-vinyl]-phenylamine

A mixture of 10.1 g (40 mmol) of (E)-1-methoxy-4-[2-(4-nitrophenyl)ethenyl]-benzene in 70 ml of ethanol and 130 ml of hydrochloric acid (25%) is heated to 110° C. Portionwise, 15 g of tin are added and stirring is continued for 4.5 hours at 110° C. For the working-up, the reaction mixture is cooled and neutralised with a solution of sodium hydroxide. The mixture is transferred to a separatory funnel where it is extracted with dichloromethane. The organic layer is separated, dried over sodium sulfate and evaporated. The residue is triturated in ether and, thereafter, the remaining solid is collected on a filter funnel. There are obtained 6.15 g (69% of theory) of (E)-4-[2-(4-methoxy-phenyl)-vinyl]-phenylamine as a yellow crystals; MS: m/e=226 (M+H)+.

c) (RS)-(E)-1-{4-[2-(4-Methoxy-phenyl)-vinyl]-phenyl}-5-oxo-pyrrolidine-3-carboxylic acid In an analogous manner to that described in Example 36 c), the reaction of (E)-4-[2-(4-methoxy-phenyl)-vinyl]-phenylamine with itaconic acid yields the (RS)-(E)-1-{4-[2-(4-methoxy-phenyl)-vinyl]-phenyl}-5-oxo-pyrrolidine-3-carboxylic acid as a brown solid; MS: m/e=336 (M−H)+.

d) (RS)-(E)-1-{4-[2-(4-Methoxy-phenyl)-vinyl]-phenyl}-5-oxo-pyrrolidine-3-carboxylic acid methyl ester A solution of 700 mg (2.1 mmol) of (RS)-(E)-1-{4-[2-(4-methoxy-phenyl)-vinyl]-phenyl}-5-oxo-pyrrolidine-3-carboxylic acid in 7 ml of dichloromethane and 0.7 ml of methanol is treated with 1 drop of sulfuric acid and heated at 40° C. for 20 hours. For the working-up, the solvent is evaporated, thereafter, the residue is treated with water and ethyl acetate. The organic layer is separated, dried over magnesium sulfate, and evaporated under reduced pressure. After crystallization from ether of the crude ester, 584 mg (80% of theory) of (RS)-(E)-1-{4-[2-(4-methoxy-phenyl)-vinyl]-phenyl}-5-oxo-pyrrolidine-3-carboxylic acid methyl ester are obtained as a light brown solid; MS: m/e=352 (M+H)+.

e) (RS)-(E)-1-{4-[2-(4-Methoxy-phenyl)-vinyl]-phenyl}-5-oxo-pyrrolidine-3-carboxylic acid methylamide A solution of 400 mg (1.1 mmol) of (RS)-(E)-1-{4-[2-(4-methoxy-phenyl)-vinyl]-phenyl}-5-oxo-pyrrolidine-3-carboxylic acid methyl ester in 1.4 ml of a solution of methylamine in ethanol (33%) is heated at 90° C. for 18 h in a sealed vial. For the working-up, the cooled solution is treated with water to precipitate the product. The solid material is collected on a filter funnel, washed with water, finally, with heptane. After crystallization of the crude amide from a mixture of N,N-dimethylformamide and methanol, 98 mg (25% of theory) of (RS)-(E)-1-{4-[2-(4-methoxy-phenyl)-vinyl]-phenyl}-5-oxo-pyrrolidine-3-carboxylic acid methylamide are obtained as a light brown solid; MS: m/e=351 (M+H)+.

EXAMPLE 38

(RS)-(E)-1-{4-[2-(3-Methoxy-phenyl)-vinyl]-phenyl}-5-oxo-pyrrolidine-3-carboxylic acid methylamide a) (E)-1-Methoxy-3-[2-(4-nitrophenyl)ethenyl]-benzene In an analogous manner to that described in Example 36a), the reaction of diethyl (4-nitrobenzyl)phosphonate with 3-methoxybenzaldehyde yields the (E)-1-methoxy-3-[2-(4-nitrophenyl)ethenyl]-benzene as a yellow solid; MS: m/e=255 (M+H)+.

b) (E)-4-[2-(3-Methoxy-phenyl)-vinyl]-phenylamine

In an analogous manner to that described in Example 37b), the reduction of (E)-1-methoxy-3-[2-(4-nitrophenyl)ethenyl]-benzene using tin yields the (E)-4-[2-(3-methoxy-phenyl)-vinyl]-phenylamine as a brown oil; MS: m/e=226 (M+H)+.

c) (RS)-(E)-1-{4-[2-(3-Methoxy-phenyl)-vinyl]-phenyl}-5-oxo-pyrrolidine-3-carboxylic acid In an analogous manner to that described in Example 36 c), the reaction of (E)-4-[2-(3-methoxy-phenyl)-vinyl]-phenylamine with itaconic acid yields the (RS)-(E)-1-{4-[2-(3-methoxy-phenyl)-vinyl]-phenyl}-5-oxo-pyrrolidine-3-carboxylic acid as a brown solid; MS: m/e=336 (M−H)+.

d) (RS)-(E)-1-{4-[2-(3-Methoxy-phenyl)-vinyl]-phenyl}-5-oxo-pyrrolidine-3-carboxylic acid methyl ester In an analogous manner to that described in Example 37 d), the esterification of (RS)-(E)-1-{4-[2-(3-methoxy-phenyl)-vinyl]-phenyl}-5-oxo-pyrrolidine-3-carboxylic acid yields the (RS)-(E)-1-{4-[2-(3-methoxy-phenyl)-vinyl]-phenyl}-5-oxo-pyrrolidine-3-carboxylic acid methyl ester as a brown solid; MS: m/e=352 (M+H)+.

e) (RS)-(E)-1-{4-[2-(3-Methoxy-phenyl)-vinyl]-phenyl}-5-oxo-pyrrolidine-3-carboxylic acid methylamide In an analogous manner to that described in Example 37 e), the aminolysis of (RS)-(E)-1-{4-[2-(3-methoxy-phenyl)- vinyl]-phenyl}-5-oxo-pyrrolidine-3-carboxylic acid methyl ester yields the (RS)-(E)-1-{4-[2-(3-methoxy-phenyl)-vinyl]-phenyl}-5-oxo-pyrrolidine-3-carboxylic acid methylamide as a light yellow solid; MS: m/e=351 (M+H)$^+$.

EXAMPLE 39

(RS)-(E)-1-{4-[2-(4-Fluoro-phenyl)-vinyl]-phenyl}-5-oxo-pyrrolidine-3-carboxylic acid methylamide a) (E)-1-Fluoro-4-[2-(4-nitrophenyl)ethenyl]-benzene In an analogous manner to that described in Example 36 a), the reaction of diethyl (4-nitrobenzyl)phosphonate with 4-fluorobenzaldehyde yields the (E)-1-fluoro-4-[2-(4-nitrophenyl)ethenyl]-benzene as a yellow crystalline solid; MS: m/e=243 (M)$^+$.

b) (E)-4-[2-(4-Fluoro-phenyl)-vinyl]-phenylamine

In an analogous manner to that described in Example 37 b), the reduction of (E)-1-fluoro-3-[2-(4-nitrophenyl)ethenyl]-benzene with tin yields the (E)-4-[2-(4-fluoro-phenyl)-vinyl]-phenylamine as a white solid; MS: 214 (M+H)$^+$.

c) (RS)-(E)-1-{4-[2-(4-Fluoro-phenyl)-vinyl]-phenyl}-5-oxo-pyrrolidine-3-carboxylic acid In an analogous manner to that described in Example 36 c), the reaction of (E)-4-[2-(4-fluoro-phenyl)-vinyl]-phenylamine with itaconic acid yields the (RS)-(E)-1-{4-[2-(4-fluoro-phenyl)-vinyl]-phenyl}-5-oxo-pyrrolidine-3-carboxylic acid which was directly engaged in the next step without further purification and characterisation.

d) (RS)-(E)-1-{4-[2-(4-Fluoro-phenyl)-vinyl]-phenyl}-5-oxo-pyrrolidine-3-carboxylic acid methyl ester In an analogous manner to that described in Example 37 d), the esterification of (RS)-(E)-1-{4-[2-(4-fluoro-phenyl)-vinyl]-phenyl}-5-oxo-pyrrolidine-3-carboxylic acid yields the (RS)-(E)-1-{4-[2-(4-fluoro-phenyl)-vinyl]-phenyl}-5-oxo-pyrrolidine-3-carboxylic acid methyl ester.

e) (RS)-(E)-1-{4-[2-(4-Fluoro-phenyl)-vinyl]-phenyl}-5-oxo-pyrrolidine-3-carboxylic acid methylamide In an analogous manner to that described in Example 37 e), the aminolysis of (RS)-(E)-1-{4-[2-(4-fluoro-phenyl)-vinyl]-phenyl}-5-oxo-pyrrolidine-3-carboxylic acid methyl ester yields the (RS)-(E)-1-{4-[2-(4-fluoro-phenyl)-vinyl]-phenyl}-5-oxo-pyrrolidine-3-carboxylic acid methylamide as a white solid; MS: m/e=339 (M+H)$^+$.

EXAMPLE 40

(RS)-1-{4-[2-(3-Chloro-phenyl)-ethyl]-phenyl}-5-oxo-pyrrolidine-3-carboxylic acid methylamide a) (E)-1-Chloro-3-[2-(4-nitrophenyl)ethenyl]-benzene In an analogous manner to that described in Example 36 a), the reaction of diethyl (4-nitrobenzyl)phosphonate with 3-chlorobenzaldehyde yields the (E)-1-chloro-3-[2-(4-nitrophenyl)ethenyl]-benzene as an orange crystalline solid; MS: m/e=259 (M)$^+$.

b) 4-[2-(3-Chloro-phenyl)-ethyl]-phenylamine

In an analogous manner to that described in Example 36 b), the hydrogenation of (E)-1-chloro-3-[2-(4-nitrophenyl)ethenyl]-benzene using platinum on carbon (5%) as the catalyst but with a reaction time of 18 hours and simultaneous reduction of the double bond yields the 4-[2-(3-chloro-phenyl)-ethyl]-phenylamine as a dark brown oil; MS: m/e=232 (M+H)$^+$.

c) (RS)-1-{4-[2-(3-Chloro-phenyl)-ethyl]-phenyl}-5-oxo-pyrrolidine-3-carboxylic acid In an analogous manner to that described in Example 36 c), the reaction of 4-[2-(3-chloro-phenyl)-ethyl]-phenylamine with itaconic acid yields the (RS)-1-{4-[2-(3-chloro-phenyl)-ethyl]-phenyl}-5-oxo-pyrrolidine-3-carboxylic acid as an off-white solid; MS: m/e=342 (M–H)$^+$.

d) (RS)-1-{4-[2-(3-Chloro-phenyl)-ethyl]-phenyl}-5-oxo-pyrrolidine-3-carboxylic acid methyl ester In an analogous manner to that described in Example 37 d), the esterification of (RS)-1-{4-[2-(3-chloro-phenyl)-ethyl]-phenyl}-5-oxo-pyrrolidine-3-carboxylic acid yields the (RS)-1-{4-[2-(3-chloro-phenyl)-ethyl]-phenyl}-5-oxo-pyrrolidine-3-carboxylic acid methyl ester as a white solid; MS: m/e=358 (M+H)$^+$.

e) (RS)-(E)-1-{4-[2-(3-Chloro-phenyl)-vinyl]-phenyl}-5-oxo-pyrrolidine-3-carboxylic acid methylamide In an analogous manner to that described in Example 37 e), the aminolysis of (RS)-1-{4-[2-(3-chloro-phenyl)-ethyl]-phenyl}-5-oxo-pyrrolidine-3-carboxylic acid methyl ester yields the (RS)-1-{4-[2-(3-chloro-phenyl)-ethyl]-phenyl}-5-oxo-pyrrolidine-3-carboxylic acid methylamide as a light yellow solid; MS: m/e=357 (M+H)$^+$.

EXAMPLE 41

(RS)-1-{4-[2-(4-Chloro-phenyl)-ethyl]-phenyl}-5-oxo-pyrrolidine-3-carboxylic acid methylamide a) (E)-1-Chloro-4-[2-(4-nitrophenyl)ethenyl]-benzene In an analogous manner to that described in Example 36 a), the reaction of diethyl (4-nitrobenzyl)phosphonate with 4-chlorobenzaldehyde yields the (E)-1-chloro-4-[2-(4-nitrophenyl)ethenyl]-benzene as an yellow crystalline solid; MS: m/e=259 (M)$^+$.

b) 4-[2-(4-Chloro-phenyl)-ethyl]-phenylamine

In an analogous manner to that described in Example 36 b), the hydrogenation of (E)-1-chloro-4-[2-(4-nitrophenyl)ethenyl]-benzene using platinum on carbon (5%) as the catalyst but with a reaction time of 18 hours and simultaneous reduction of the double bond yields the 4-[2-(4-chloro-phenyl)-ethyl]-phenylamine as a light yellow solid; MS: m/e=232 (M+H)$^+$.

c) (RS)-1-{4-[2-(4–Chloro-phenyl)-ethyl]-phenyl}-5-oxo-pyrrolidine-3-carboxylic acid In an analogous manner to that described in Example 36 c), the reaction of 4-[2-(4-chloro-phenyl)-ethyl]-phenylamine with itaconic acid yields the (RS)-1-{4-[2-(4-chloro-phenyl)-ethyl]-phenyl}-5-oxo-pyrrolidine-3-carboxylic acid as an off-white solid; MS: m/e=342 (M–H)$^+$.

d) (RS)-1-{4-[2-(4–Chloro-phenyl)-ethyl]-phenyl}-5-oxo-pyrrolidine-3-carboxylic acid methyl ester In an analogous manner to that described in Example 37 d), the esterification of (RS)-1-{4-[2-(4-chloro-phenyl)-ethyl]-phenyl}-5-oxo-pyrrolidine-3-carboxylic acid yields the (RS)-1-{4-[2-(4-chloro-phenyl)-ethyl]-phenyl}-5-oxo-pyrrolidine-3-carboxylic acid methyl ester as a white solid; MS: m/e=357 (M)$^+$.

e) (RS)-(E)-1-{4-[2-(4–Chloro-phenyl)-vinyl]-phenyl}-5-oxo-pyrrolidine-3-carboxylic acid methylamide In an analogous manner to that described in Example 37 e), the aminolysis of (RS)-1-{4-[2-(4-chloro-phenyl)-ethyl]-phenyl}-5-oxo-pyrrolidine-3-carboxylic acid methyl ester yields the (RS)-1-{4-[2-(4-chloro-phenyl)-ethyl]-phenyl}-5-oxo-pyrrolidine-3-carboxylic acid methylamide as a white solid; MS: m/e=357 (M+H)$^+$.

EXAMPLE 42

(RS)-1-{4-[2-(3-Fluoro-phenyl)-ethyl]-phenyl}-5-oxo-pyrrolidine-3-carboxylic acid methylamide a) 4-[2-(3-Fluoro-phenyl)-ethyl]-phenylamine In an analogous manner to that described in Example 36 b), the hydrogenation of (E)-1-fluoro-3-[2-(4-nitrophenyl)ethenyl]-benzene [Example 36 a)] using palladium on carbon (10%) as the catalyst yields the 4-[2-(3-fluoro-phenyl)-ethyl]-phenylamine as a yellow solid; MS: m/e=215 (M)$^+$.

b) (RS)-1-{4-[2-(3-Fluoro-phenyl)-ethyl]-phenyl}-5-oxo-pyrrolidine-3-carboxylic acid In an analogous manner to that described in Example 36 c), the reaction of 4-[2-(3-fluoro-phenyl)-ethyl]-phenylamine with itaconic acid yields the (RS)-1-{4-[2-(3-fluoro-phenyl)-ethyl]-phenyl}-5-oxo-pyrrolidine-3-carboxylic acid as a light brown solid; MS: m/e=326 (M–H)$^+$.

c) (RS)-(E)-1-{4-[2-(3-Fluoro-phenyl)-vinyl]-phenyl}-5-oxo-pyrrolidine-3-carboxylic acid methylamide In an analogous manner to that described in Example 36 d), the esterification of (RS)-1-{4-[2-(3-fluoro-phenyl)-ethyl]-phenyl}-5-oxo-pyrrolidine-3-carboxylic acid and reaction of the intermediate acid chloride with methylamine yields the (RS)-1-{4-[2-(3-fluoro-phenyl)-ethyl]-phenyl}-5-oxo-pyrrolidine-3-carboxylic acid methylamide as a light yellow solid; MS: m/e=341 (M+H)$^+$.

EXAMPLE 43

(RS)-1-{4-[2-(4-Fluoro-phenyl)-ethyl]-phenyl}-5-oxo-pyrrolidine-3-carboxylic acid methylamide a) 4-[2-(4-Fluoro-phenyl)-ethyl]-phenylamine In an analogous manner to that described in Example 36 b), the hydrogenation of (E)-1-fluoro-4-[2-(4-nitrophenyl)ethenyl]-benzene [Example 39 a)] using palladium on carbon (10%) as the catalyst yields the 4-[2-(4-fluoro-phenyl)-ethyl]-phenylamine as a light red solid; MS: n/e=216 (M+H)$^+$.

b) (RS)-1-{4-[2-(4-Fluoro-phenyl)-ethyl]-phenyl}-5-oxo-pyrrolidine-3-carboxylic acid In an analogous manner to that described in Example 36 c), the reaction of 4-[2-(4-fluoro-phenyl)-ethyl]-phenylamine with itaconic acid yields the (RS)-1-{4-[2-(4-fluoro-phenyl)-ethyl]-phenyl}-5-oxo-pyrrolidine-3-carboxylic acid as a white solid; MS: m/e=326 (M–H)$^+$.

c) (RS)-1-{4-[2-(4-Fluoro-phenyl)-ethyl]-phenyl}-5-oxo-pyrrolidine-3-carboxylic acid methyl ester In an analogous manner to that described in Example 37 d), the esterification of (RS)-1-{4-[2-(4-fluoro-phenyl)-ethyl]-phenyl}-5-oxo-pyrrolidine-3-carboxylic acid yields the (RS)-1-{4-[2-(4-fluoro-phenyl)-ethyl]-phenyl}-5-oxo-pyrrolidine-3-carboxylic acid methyl ester as a white solid; MS: m/e=342 (M+H)$^+$.

d) (RS)-(E)-1-{4-[2-(4-Fluoro-phenyl)-vinyl]-phenyl}-5-oxo-pyrrolidine-3-carboxylic acid methylamide In an analogous manner to that described in Example 37 e), the aminolysis of (RS)-1-{4-[2-(4-fluoro-phenyl)-ethyl]-phenyl}-5-oxo-pyrrolidine-3-carboxylic acid methyl ester yields the (RS)-1-{4-[2-(4-fluoro-phenyl)-ethyl]-phenyl}-5-oxo-pyrrolidine-3-carboxylic acid methylamide as a light brown solid; MS: m/e=341 (M+H)$^+$.

EXAMPLE 44

(RS)-1-{4-[2-(3Methoxy-phenyl)-ethyl]-phenyl}-5-oxo-pyrrolidine-3-carboxylic acid methylamide a) 4-[2-(3-Methoxy-phenyl)-ethyl]-phenylamine In an analogous manner to that described in Example 36 b), the hydrogenation of (E)-1-fluoro-4-[2-(4-nitrophenyl)ethenyl]-benzene [Example 38 a)] using palladium on carbon (10%) as the catalyst yields the 4-[2-(3-methoxy-phenyl)-ethyl]-phenylamine as a light red solid; MS: m/e=228 (M+H)$^+$.

b) (RS)-1-{4-[2-(3-Methoxy-phenyl)-ethyl]-phenyl}-5-oxo-pyrrolidine-3-carboxylic acid In an analogous manner to that described in Example 36 c), the reaction of 4-[2-(3-methoxy-phenyl)-ethyl]-phenylamine with itaconic acid yields the (RS)-1-{4-[2-(3-methoxy-phenyl)-ethyl]-phenyl}-5-oxo-pyrrolidine-3-carboxylic acid as a white solid; MS: m/e=338 (M–H)$^+$.

c) (RS)-1-{4-[2-(3Methoxy-phenyl)-ethyl]-phenyl}-5-oxo-pyrrolidine-3-carboxylic acid methyl ester In an analogous manner to that described in Example 37 d), the esterification of (RS)-1-{4-[2-(3-methoxy-phenyl)-ethyl]-phenyl}-5-oxo-pyrrolidine-3-carboxylic acid yields the (RS)-1-{4-[2-(3-methoxy-phenyl)-ethyl]-phenyl}-5-oxo-pyrrolidine-3-carboxylic acid methyl ester as a light yellow oil; MS: m/e=354 (M+H)$^+$.

d) (RS)-(E)-1-{4-[2-(3-Methoxy-phenyl)-ethyl]-phenyl}-5-oxo-pyrrolidine-3-carboxylic acid methylamide In an analogous manner to that described in Example 37 e), the aminolysis of (RS)-1-{4-[2-(3-methoxy-phenyl)-ethyl]-phenyl}-5-oxo-pyrrolidine-3-carboxylic acid methyl ester yields the (RS)-1-{4-[2-(3-methoxy-phenyl)-ethyl]-phenyl}-5-oxo-pyrrolidine-3-carboxylic acid methylamide as a white solid; MS: m/e=353 (M+H)$^+$.

EXAMPLE 45

(RS)-1-[6-(4-Fluoro-benzyloxy)-pyridin-3-yl]-5-oxo-pyrrolidine-3-carboxylic acid methylamide a) 2-(4-Fluoro-benzyloxy)-5-nitro-pyridine In an analogous manner to that described in J. Medicinal Chem. 33:2087–93 (1990), the reaction 4-fluorobenzylalcohol instead of benzylalcohol with 2-chloro-5-nitropyridine yields the 2-(4-fluoro-benzyloxy)-5-nitro-pyridine as a yellow solid.

b) 6-(4-Fluoro-benzyloxy)-pyridin-3-ylamine

A mixture of 0.70 g (2.8 mmol) of 2-(4-fluoro-benzyloxy)-5-nitro-pyridine and 2.36 g (4.2 mmol) of iron powder in 35 ml of water and 0.7 ml of acetic acid is heated under reflux for 4 hours. For the working-up, the reaction mixture is treated under vigorous stirring with water and ethyl acetate, thereafter, filtered over a layer of Dicalit. The organic layer is separated, dried over sodium sulfate and evaporated under reduced pressure. There are obtained 0.28 g (45% of theory) of 6-(4-fluoro-benzyloxy)-pyridin-3-ylamine as a greenish solid which is engaged in the next step without further purification.

c) (RS)-1-[6-(4-Fluoro-benzyloxy)-pyridin-3-yl]-5-oxo-pyrrolidine-3-carboxylic acid In an analogous manner to that described in Example 36 c), the reaction of 6-(4-fluoro-benzyloxy)-pyridin-3-ylamine with itaconic acid yields the crude (RS)-1-[6-(4-fluoro-benzyloxy)-pyridin-3-yl]-5-oxo-pyrrolidine-3-carboxylic acid as a green solid (yield 47% of theory).

d) (RS)-1-[6-(4-Fluoro-benzyloxy)-pyridin-3-yl]-5-oxo-pyrrolidine-3-carboxylic acid methylamide A solution of 105 mg (0.3 mmol) of (RS)-1-[6-(4-fluoro-benzyloxy)-pyridin-3-yl]-5-oxo-pyrrolidine-3-carboxylic acid in 5 ml N,N-dimethylformamide is treated with 58 mg (0.35 mmol) of N,N-carbonyl-diimidazole, and the mixture is stirred at RT for 15 min. Thereafter, 26 mg (0.38 mmol) of methylamine hydrochloride and 50 µl (0.35 mmol) of triethylamine are added. After 30 min, the solvent is evaporated under reduced pressure and the residue is chromatographed on silica gel using a 98:2-mixture of dichloromethane and methanol as the eluent. There are obtained 15 mg (15% of theory) of (RS)-1-[6-(4-fluoro-benzyloxy)-pyridin-3-yl]-5-oxo-pyrrolidine-3-carboxylic acid methylamide as a green oil which solidifies on standing. MS: m/e=344 (M+H)$^+$.

The following Examples A to D are prophetic.

EXAMPLE A

Tablets

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

Injection Solution

An injection solution may have the following composition and is manufactured in usual manner:

| | |
|---|---|
| Active substance | 1.0 mg |
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

The invention claimed is:

1. A compound of the formula I

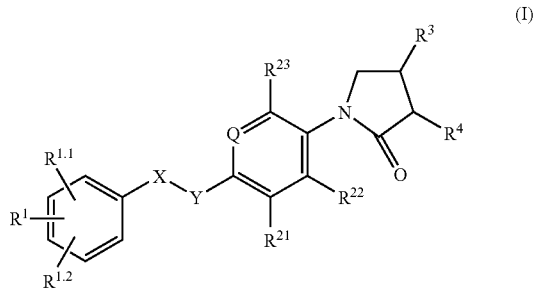

wherein

Q is =N—;

X—Y is —CH$_2$—CH$_2$—, —CH=CH— or —CH$_2$—O—;

R$^1$, R$^{1.1}$ and R$^{1.2}$ independently from each other are selected from the group consisting of hydrogen, halogen, (C$_1$–C$_6$)-alkyl, halogen-(C$_1$–C$_6$)-alkyl, cyano, (C$_1$–C$_6$)-alkoxy or halogen-(C$_1$–C$_6$)-alkoxy;

R$^{21}$, R$^{22}$ and R$^{23}$ independently from each other are selected from the group consisting of hydrogen and halogen;

R$^{24}$ is hydrogen, halogen or methyl;

R$^3$ is —C(O)N(H)CH$_3$ or —CH$_2$CN; and

R$^4$ is hydrogen;

or an individual isomer or racemic or non-racemic mixture thereof.

2. A compound according to claim 1 wherein —X—Y— is —CH$_2$—O—; R$^1$, R$^{1.1}$, and R$^{1.2}$ independently are selected from the group consisting of hydrogen, halogen, methyl, halogenmethyl, cyano, methoxy, and halogenmethoxy; R$^{21}$, R$^{22}$, and R$^{23}$ are hydrogen; and R$^3$ is —C(O)N(H)CH$_3$.

3. A compound of claim 1 wherein X—Y is —CH$_2$—O—.

4. A compound according to claim 1 wherein R$^3$ is —C(O)N(H)CH$_3$.

5. A compound according to claim 1 wherein R$^3$ is CH$_2$CN.

6. A compound according to claim 1 wherein X—Y is —CH$_2$—CH$_2$— or —CH=CH—.

7. A compound according to claim 1 wherein R$^{21}$, R$^{22}$, and R$^{23}$ are hydrogen.

8. A compound according to claim 1 wherein R$^{21}$ and R$^{23}$ are hydrogen and R$^{22}$ is fluoro.

9. A compound according to claim 1 wherein R$^{1.1}$ and R$^{1.2}$ are hydrogen and R$^1$ is selected from fluoro, chloro, halogenmethyl, cyano, methoxy, and halogenmethoxy.

10. A compound according to claim 1 wherein R$^1$, R$^{1.1}$ and R$^{1.2}$ independently from each other are selected from the group consisting of hydrogen, halogen, methyl, halogenmethyl, cyano, methoxy or halogen-methoxy.

11. A compound according to claim 1 wherein R$^1$, R$^{1.1}$, and R$^{1.2}$ are halogen.

12. A compound according to claim 11 wherein R$^1$, R$^{1.1}$, and R$^{1.2}$ are fluoro.

13. A compound according to claim 12 wherein R$^1$, R$^{1.1}$, and R$^{1.2}$ are 2,4,6-trifluoro; 2,4,5-trifluoro; 2,3,6-trifluoro; 2,3,4-trifluoro; or 3,4,5-trifluoro.

14. A compound according to claim 1 wherein R$^{1.2}$ is hydrogen and R$^1$ and R$^{1.1}$ independently from each other are selected from the group consisting of hydrogen, halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy.

15. A compound according to claim 14 wherein R$^1$ and R$^{1.1}$ independently are halogen or (C$_1$–C$_6$)-alkyl.

16. A compound according to claim 15 wherein R$^{1.1}$ is halogen and R$^1$ is halogen or (C$_1$–C$_6$)-alkyl.

17. A compound according to claim 1 wherein R$^1$, R$^{1.1}$, and R$^{1.2}$ are hydrogen.

18. A compound according to claim 1 wherein R$^{1.1}$ and R$^{1.2}$ are hydrogen and R$^1$ is selected from halogen, cyano, (C$_1$–C$_6$)-alkyl, halogen-(C$_1$–C$_6$)-alkyl, (C$_1$–C$_6$)-alkoxy or halogen-(C$_1$–C$_6$)-alkoxy.

19. A compound according to claim 18 wherein R$^1$ is halogen, methyl, halogenmethyl, cyano, methoxy, and halogenmethoxy.

20. A compound according to claim 19 wherein R$^1$ is fluoro.

21. A compound according to claim 20 wherein R$^1$ is 3-fluoro or 4-fluoro.

22. A compound according to claim 19 wherein R$^1$ is chloro.

23. A compound according to claim 22 wherein R$^1$ is 3-chloro.

24. A compound according to claim 19 wherein R$^1$ is halogenmethyl.

25. A compound according to claim 24 wherein R$^1$ is 3-trifluoromethyl.

26. A compound according to claim 19 wherein R$^1$ is cyano.

27. A compound according to claim 19 wherein R$^1$ is methoxy.

28. A compound according to claim 27 wherein R$^1$ is 2-methoxy, 3-methoxy, or 4-methoxy.

29. A compound according to claim 19 wherein R$^1$ is halogenmethoxy.

30. A compound according to claim 29 wherein R$^1$ is 3-trifluoromethoxy.

31. A compound according to claim 1 wherein the compound has (R)-configuration.

32. A compound which is (RS)-1-[6-(4-fluoro-benzyloxy)-pyridin-3-yl]-5-oxo-pyrrolidine-3-carboxylic acid methylamide.

33. A composition comprising a compound of formula I

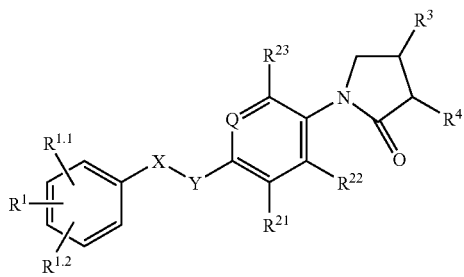

(I)

wherein
Q is =N—;
X—Y is —CH$_2$—CH$_2$—, —CH=CH— or —CH$_2$—O—;
R$^1$, R$^{1.1}$ and R$^{1.2}$ independently from each other are selected from the group consisting of hydrogen, halogen, (C$_1$–C$_6$)-alkyl, halogen-(C$_1$–C$_6$)-alkyl, cyano, (C$_1$–C$_6$)-alkoxy or halogen-(C$_1$–C$_6$)-alkoxy;
R$^{21}$, R$^{22}$ and R$^{23}$ independently from each other are selected from the group consisting of hydrogen and halogen;
R$^{24}$ is hydrogen, halogen or methyl;
R$^3$ is —C(O)N(H)CH$_3$ or —CH$_2$CN; and
R$^4$ is hydrogen;
or an individual isomer or racemic or non-racemic mixture thereof, and a pharmaceutically acceptable carrier.

* * * * *